(12) United States Patent
Zhang

(10) Patent No.: US 11,136,334 B2
(45) Date of Patent: Oct. 5, 2021

(54) SOLID FORMS OF 3-(5-FLUOROBENZOFURAN-3-YL)-4-(5-METHYL-5H-[1,3]DIOXOLO[4,5-F]INDOL-7-YL)PYRROLE-2,5-DIONE

(71) Applicant: Actuate Therapeutics Inc., Fort Worth, TX (US)

(72) Inventor: Yamin Zhang, Beijing (CN)

(73) Assignee: ACTUATE THERAPEUTICS INC., Fort Worth, TX (US)

( * ) Notice: Subject to any disclaimer, the term of this patent is extended or adjusted under 35 U.S.C. 154(b) by 0 days.

(21) Appl. No.: 16/638,303

(22) PCT Filed: Aug. 10, 2018

(86) PCT No.: PCT/US2018/046203
§ 371 (c)(1),
(2) Date: Feb. 11, 2020

(87) PCT Pub. No.: WO2019/032958
PCT Pub. Date: Feb. 14, 2019

(65) Prior Publication Data
US 2020/0223861 A1 Jul. 16, 2020

Related U.S. Application Data

(60) Provisional application No. 62/544,277, filed on Aug. 11, 2017.

(51) Int. Cl.
*C07D 491/056* (2006.01)
*A61P 35/00* (2006.01)
(52) U.S. Cl.
CPC ......... *C07D 491/056* (2013.01); *A61P 35/00* (2018.01); *C07B 2200/13* (2013.01)

(58) Field of Classification Search
CPC . A61P 35/00; C07B 2200/13; C07D 491/056; C07D 498/04
See application file for complete search history.

(56) References Cited

U.S. PATENT DOCUMENTS 8,207,216 B2   6/2012  Kozikowski et al.

FOREIGN PATENT DOCUMENTS

WO    2008077138 A1    6/2008

OTHER PUBLICATIONS

Gaistina, et al, "From a Natural Product Lead to the Identification of Potent and Selective Benzofuran-3-yl-(indol-3-yl)maleimides As Glycogen Synthase Kinase 3B Inhibitors That Suppress Proliferation and Survival of Pancreatic Cancer Cells", J. Med. Chem., 2009, 52, 1853-1863.
K Pal, et al, "Inhibition of GSK-3 Induces Differentiation and Impaired Metabolism in Renal Cancer, Molecular Cancer Therapeutics", vol. 13, No. 2, Dec. 10, 2013, pp. 285-296.
S. Hillard, et al., Glycogen Synthase Kinase 3B Inhibitors Induce Apoptosis in Ovarian Cancer Cells and Inhibit In Vivo Tumor Growth, Anti Cancer Drugs, 2011, 22, 978-985 (Abstract provided).
International Search Report and Written Opinion issued in PCT/US2018/046203 dated Nov. 19, 2018.

*Primary Examiner* — Savitha M Rao
(74) *Attorney, Agent, or Firm* — BakerHostetler

(57) ABSTRACT

The present disclosure relates to solid forms of 3-(5-Fluorobenzofuran-3-yl)-4-(5-methyl-5H-[1,3]dioxolo[4,5-f]indol-7-yl)pyrrole-2,5-dione, processes for preparation thereof, pharmaceutical compositions thereof, and uses thereof in treating disease.

17 Claims, 22 Drawing Sheets

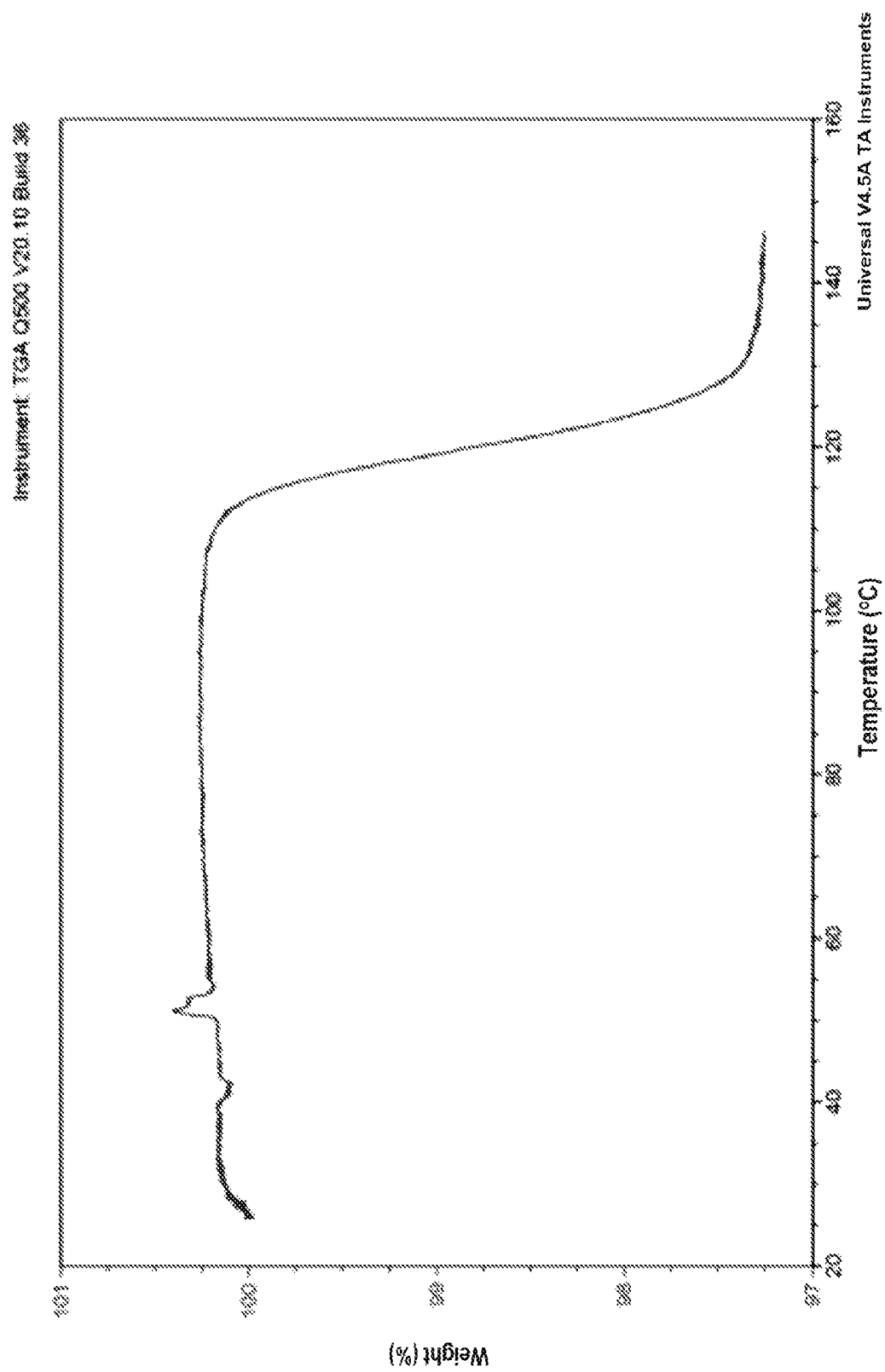

SOLID FORMS OF 3-(5-FLUOROBENZOFURAN-3-YL)-4-(5-METHYL-5H-[1,3]DIOXOLO [4,5-F]INDOL-7-YL)PYRROLE-2,5-DIONE

CROSS-REFERENCE TO RELATED APPLICATIONS

This application is the National Stage Application of International Patent Application No. PCT/US2018/046203, filed Aug. 10, 2018 which claims the benefit of priority to U.S. Provisional Application No. 62/544,277, filed on Aug. 11, 2017. The entirety of each of these applications is incorporated by reference herein.

FIELD OF THE DISCLOSURE

The present disclosure relates to solid forms of 3-(5-Fluorobenzofuran-3-yl)-4-(5-methyl-5H-[1,3]dioxolo[4,5-f]indol-7-yl)pyrrole-2,5-dione, processes for preparation thereof, pharmaceutical compositions thereof, and uses thereof in treating disease.

BACKGROUND OF THE DISCLOSURE 3-(5-Fluorobenzofuran-3-yl)-4-(5-methyl-5H-[1,3]dioxolo[4,5-f]indol-7-yl)pyrrole-2,5-dione ("9-ING-41") has the following chemical structure:

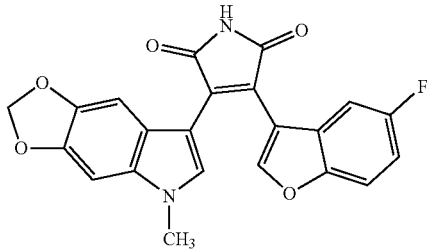 [SMILES: Cn1cc(C2=C(c3coc4ccc(F)cc34)C(=O)NC2=O)c2cc3c(cc21)OCO3]

9-ING-41 has been reported as being useful for the treatment of cancers, including brain, lung, breast, ovarian, bladder, neuroblastoma, renal, and pancreatic cancers, as well as for treatment of traumatic brain injury.

The structure, properties, and/or biological activity of 9-ING-41 are set forth in U.S. Pat. No. 8,207,216; Gaisina et al., From a Natural Product Lead to the Identification of Potent and Selective Benzofuran-3-yl-(indol-3-yl)maleimides as Glycogen Synthase Kinase 3β Inhibitors That Suppress Proliferation and Survival of Pancreatic Cancer Cells, *J. Med. Chem.* 2009, 52, 1853-1863; and Hilliard, et al., Glycogen synthase kinase 3β inhibitors induce apoptosis in ovarian cancer cells and inhibit in-vivo tumor growth, *Anti-Cancer Drugs* 2011, 22:978-985.

There is a need for novel solid forms (including polymorphs and solvates) of 9-ING-41.

SUMMARY OF THE DISCLOSURE

The present disclosure relates to solid forms of 9-ING-41, processes for preparing solid forms of 9-ING-41, pharmaceutical compositions comprising solid forms of 9-ING-41, and methods of treatment comprising administering solid forms of 9-ING-41.

In some aspects, the present disclosure is directed to a solid form which is crystalline Form I of 3-(5-fluorobenzofuran-3-yl)-4-(5-methyl-5H-[1,3]dioxolo[4,5-f]indol-7-yl)pyrrole-2,5-dione ("9-ING-41"). In other aspects, the present disclosure is directed to a solid form which is Solvate 1, Solvate 2, Solvate 3, Solvate 4, Solvate 5, Solvate 6, Solvate 7, Solvate 8, or Solvate 9 of 3-(5-fluorobenzofuran-3-yl)-4-(5-methyl-5H-[1,3]dioxolo[4,5-f]indol-7-yl)pyrrole-2,5-dione ("9-ING-41"). In yet other aspects, the present disclosure is directed to amorphous 3-(5-fluorobenzofuran-3-yl)-4-(5-methyl-5H-[1,3]dioxolo[4,5-f]indol-7-yl)pyrrole-2,5-dione ("9-ING-41").

The present disclosure also provides processes for preparing solid forms of 9-ING-41.

The present disclosure also provides pharmaceutical compositions comprising the solid forms of 9-ING-41, as well as methods of their preparation.

The present disclosure also provides methods of treating disease comprising administering to a patient in need thereof a therapeutically effective amount of a disclosed solid form of 9-ING-41.

BRIEF DESCRIPTION OF THE FIGURES

FIG. 22 shows a thermogravimetric analysis (TGA) profile of 9-ING-41 Solvate 5.

DETAILED DESCRIPTION OF THE INVENTION

Figure 1:
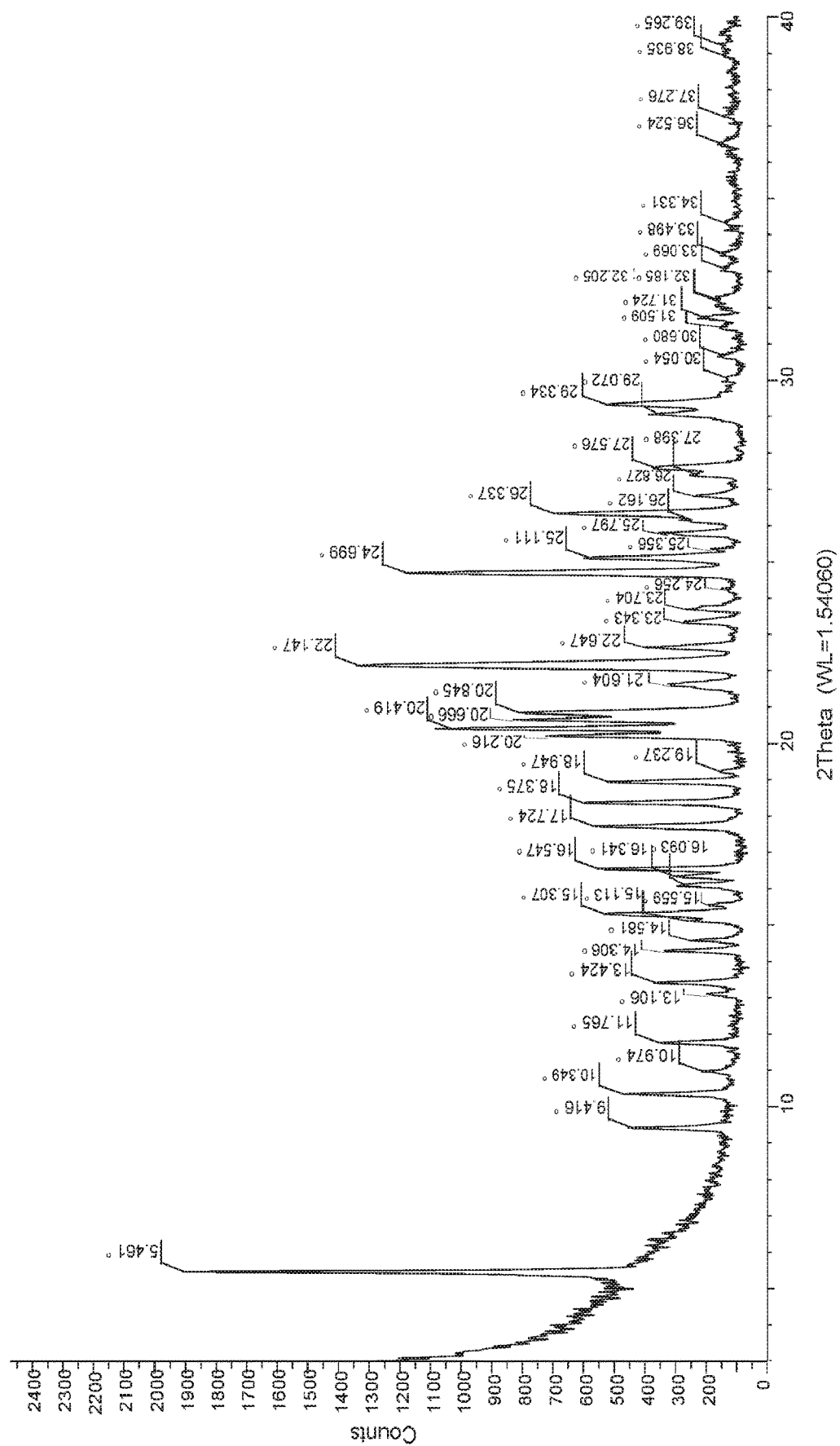
FIG. 1 shows an X-ray powder diffractogram (XRPD) of Form I of 9-ING-41.

The present disclosure relates to solid forms of 9-ING-41, processes for preparation thereof and pharmaceutical compositions comprising the solid state forms. The disclosure also relates to the conversion of the described solid state forms of 9-ING-41 to other solid state forms of 9-ING-41, 9-ING-41 salts and their solid state forms thereof.

The name "9-ING-41" is another name for 3-(5-Fluorobenzofuran-3-yl)-4-(5-methyl-5H-[1,3]dioxolo[4,5-f]indol-7-yl)pyrrole-2,5-dione, which is another name for 3-(5-fluoro-1-benzofuran-3-yl)-4-[5-methyl-2H,5H-[1,3]dioxolo[4,5-f]indol-7-yl]-2,5-dihydro-1H-pyrrole-2,5-dione. These names are used interchangeably herein.

The solid state forms of 9-ING-41 according to the present disclosure may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, or bulk density.

A crystal form may be referred to herein as being characterized by graphical data "as shown in" a Figure. Such data include, for example, powder X-ray diffractograms (XRPD), Differential Scanning Calorimetry (DSC) thermograms, thermogravimetric analysis (TGA) profiles, and dynamic vapor sorption profiles (DVS). As is well-known in the art, the graphical data potentially provides additional technical information to further define the respective solid state form which can not necessarily be described by reference to numerical values or peak positions alone. Thus, the term "substantially as shown in" when referring to graphical data in a Figure herein means a pattern that is not necessarily identical to those depicted herein, but that falls within the limits of experimental error or deviations, when considered by one of ordinary skill in the art. The skilled person would readily be able to compare the graphical data in the Figures herein with graphical data generated for an unknown crystal form and confirm whether the two sets of graphical data are characterizing the same crystal form or two different crystal forms.

A solid, crystalline form may be referred to herein as "polymorphically pure" or as "substantially free of any other form." As used herein in this context, the expression "substantially free of any other forms" will be understood to mean that the solid form contains about 20% or less, about 10% or less, about 5% or less, about 2% or less, about 1% or less, or 0% of any other forms of the subject compound as measured, for example, by XRPD. Thus, a solid form of 9-ING-41 described herein as substantially free of any other solid forms would be understood to contain greater than about 80% (w/w), greater than about 90% (w/w), greater than about 95% (w/w), greater than about 98% (w/w), greater than about 99% (w/w), or about 100% of the subject solid form of 9-ING-41. Accordingly, in some embodiments of the disclosure, the described solid forms of 9-ING-41 may contain from about 1% to about 20% (w/w), from about 5% to about 20% (w/w), or from about 5% to about 10% (w/w) of one or more other solid forms of 9-ING-41.

As used herein, unless stated otherwise, XRPD peaks reported herein are measured using CuKα radiation, λ=1.5419 Å.

The modifier "about" should be considered as disclosing the range defined by the absolute values of the two endpoints. For example, the expression "from about 2 to about 4" also discloses the range "from 2 to 4." When used to modify a single number, the term "about" refers to plus or minus 10% of the indicated number and includes the indicated number. For example, "about 10%" indicates a range of 9% to 11%, and "about 1" means from 0.9-1.1.

The term "solvate", as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

In some aspects, the present disclosure pertains to solid forms of 9-ING-41.

In some aspects, the solid form is crystalline Form I of 9-ING-41. In other aspects, the solid form is crystalline Form I of 9-ING-41 substantially free of any other solid form of 9-ING-41. Crystalline Form I of 9-ING-41 exhibits an XRPD substantially as shown in FIG. 1.

The XRPD of crystalline Form I of 9-ING-41 shown in FIG. 1 comprises reflection angles (degrees 2-theta±0.2 degrees 2-theta), line spacings (d values), and relative intensities as shown in Table 1:

TABLE 1

XRPD Data for Form I

| Angle (degrees 2-theta ± 0.2 degrees 2-theta) | d Value (Å) | Relative Intensity |
| --- | --- | --- |
| 5.461 | 16.16975 | 100.0% |
| 9.416 | 9.38533 | 20.7% |
| 10.349 | 8.54114 | 23.7% |
| 10.974 | 8.05618 | 6.6% |
| 11.765 | 7.51587 | 17.0% |
| 13.106 | 6.74962 | 7.0% |
| 13.424 | 6.59055 | 18.6% |
| 14.306 | 6.18633 | 16.7% |
| 14.581 | 6.07025 | 10.5% |
| 15.113 | 5.85758 | 10.9% |
| 15.307 | 5.78371 | 29.5% |
| 15.559 | 5.69074 | 6.8% |
| 16.093 | 5.50294 | 12.2% |
| 16.341 | 5.41993 | 14.2% |
| 16.547 | 5.35309 | 31.1% |
| 17.724 | 5.00004 | 32.1% |
| 18.375 | 4.82450 | 34.3% |
| 18.947 | 4.68011 | 28.9% |
| 19.237 | 4.61024 | 4.3% |
| 20.216 | 4.38912 | 41.6% |
| 20.419 | 4.34578 | 62.7% |
| 20.666 | 4.29443 | 48.7% |
| 20.845 | 4.25806 | 47.4% |
| 21.604 | 4.11002 | 13.6% |
| 22.147 | 4.01053 | 82.3% |
| 22.647 | 3.92307 | 19.0% |
| 23.343 | 3.80769 | 10.5% |
| 23.704 | 3.75046 | 10.7% |
| 24.256 | 3.66640 | 1.9% |
| 24.699 | 3.60160 | 72.4% |
| 25.111 | 3.54342 | 31.8% |
| 25.356 | 3.50981 | 5.0% |
| 25.797 | 3.45074 | 14.8% |
| 26.162 | 3.40351 | 9.4% |
| 26.337 | 3.38123 | 39.7% |
| 26.827 | 3.32057 | 8.6% |
| 27.398 | 3.25269 | 9.2% |
| 27.576 | 3.23208 | 18.3% |

TABLE 1-continued

XRPD Data for Form I

| Angle (degrees 2-theta ± 0.2 degrees 2-theta) | d Value (Å) | Relative Intensity |
|---|---|---|
| 29.072 | 3.06903 | 18.4% |
| 29.334 | 3.04220 | 29.5% |
| 30.054 | 2.97095 | 3.2% |
| 30.680 | 2.91180 | 4.0% |
| 31.509 | 2.83706 | 3.7% |
| 31.724 | 2.81826 | 7.5% |
| 32.185 | 2.77896 | 4.8% |
| 32.205 | 2.77725 | 4.6% |
| 33.069 | 2.70665 | 3.1% |
| 33.498 | 2.67296 | 3.9% |
| 34.331 | 2.60998 | 3.2% |
| 36.524 | 2.45820 | 3.6% |
| 37.276 | 2.41031 | 3.1% |
| 38.935 | 2.31133 | 2.3% |
| 39.265 | 2.29266 | 3.6% |
| 39.574° | 2.27544 | 2.0% |

In some embodiments of the present disclosure, crystalline Form I of 9-ING-41 is characterized by an XRPD pattern comprising a peak at one of the angles listed in Table 1. In other aspects, crystalline Form I of 9-ING-41 is characterized by an XRPD pattern comprising more than one peak at one of the angles listed in Table 1 above. In other aspects, crystalline Form I of 9-ING-41 is characterized by an XRPD pattern comprising two peaks selected from the angles listed in Table 1 above. In other aspects, crystalline Form I of 9-ING-41 is characterized by an XRPD pattern comprising three peaks selected from the angles listed in Table 1 above. In other aspects, crystalline Form I of 9-ING-41 is characterized by an XRPD pattern comprising four peaks selected from the angles listed in Table 1 above. In other aspects, crystalline Form I of 9-ING-41 is characterized by an XRPD pattern comprising five peaks selected from the angles listed in Table 1 above. In other aspects, crystalline Form I of 9-ING-41 is characterized by an XRPD pattern comprising six peaks selected from the angles listed in Table 1 above. In other aspects, crystalline Form I of 9-ING-41 is characterized by an XRPD pattern comprising seven peaks selected from the angles listed in Table 1 above. In other aspects, crystalline Form I of 9-ING-41 is characterized by an XRPD pattern comprising eight peaks selected from the angles listed in Table 1 above. In other aspects, crystalline Form I of 9-ING-41 is characterized by an XRPD pattern comprising nine peaks selected from the angles listed in Table 1 above. In other aspects, crystalline Form I of 9-ING-41 is characterized by an XRPD pattern comprising ten peaks selected from the angles listed in Table 1 above. In other aspects, crystalline Form I of 9-ING-41 is characterized by an XRPD pattern comprising more than ten peaks selected from the angles listed in Table 1 above.

In some embodiments, crystalline Form I of 9-ING-41 is characterized by an XRPD pattern comprising a peak at 5.5 degrees±0.2 degrees 2-theta. In other embodiments, crystalline Form I of 9-ING-41 is characterized by an XRPD pattern comprising peaks at 20.4, 22.1, and 24.7 degrees±0.2 degrees 2-theta. In other embodiments, crystalline Form I of 9-ING-41 is characterized by an XRPD pattern comprising peaks at 17.7, 18.4, 18.9, and 20.8 degrees±0.2 degree 2-theta. In yet other embodiments, crystalline Form I of 9-ING-41 is characterized by an XRPD pattern comprising peaks at 5.5, 9.4, 11.8, 13.4, 15.3, 24.7, and 29.3 degrees±0.2 degree 2-theta.

In some embodiments of the present disclosure, crystalline Form I of 9-ING-41 is characterized by an XRPD pattern comprising peaks at three or more of 5.5, 9.4, 11.8, 13.4, 15.3, 17.7, 18.4, 18.9, 20.4, 20.8, 22.1, 24.7, and 29.3, degrees±0.2 degrees 2-theta. In some embodiments of the present disclosure, crystalline Form I of 9-ING-41 is characterized by an XRPD pattern comprising peaks at four or more of 5.5, 9.4, 11.8, 13.4, 15.3, 17.7, 18.4, 18.9, 20.4, 20.8, 22.1, 24.7, and 29.3, degrees±0.2 degrees 2-theta. In some embodiments of the present disclosure, crystalline Form I of 9-ING-41 is characterized by an XRPD pattern comprising peaks at five or more of 5.5, 9.4, 11.8, 13.4, 15.3, 17.7, 18.4, 18.9, 20.4, 20.8, 22.1, 24.7, and 29.3, degrees±0.2 degrees 2-theta. In some embodiments of the present disclosure, crystalline Form I of 9-ING-41 is characterized by an XRPD pattern comprising peaks at six or more of 5.5, 9.4, 11.8, 13.4, 15.3, 17.7, 18.4, 18.9, 20.4, 20.8, 22.1, 24.7, and 29.3, degrees±0.2 degrees 2-theta. In some embodiments of the present disclosure, crystalline Form I of 9-ING-41 is characterized by an XRPD pattern comprising peaks at seven or more of 5.5, 9.4, 11.8, 13.4, 15.3, 17.7, 18.4, 18.9, 20.4, 20.8, 22.1, 24.7, and 29.3, degrees±0.2 degrees 2-theta.

Figure 2:
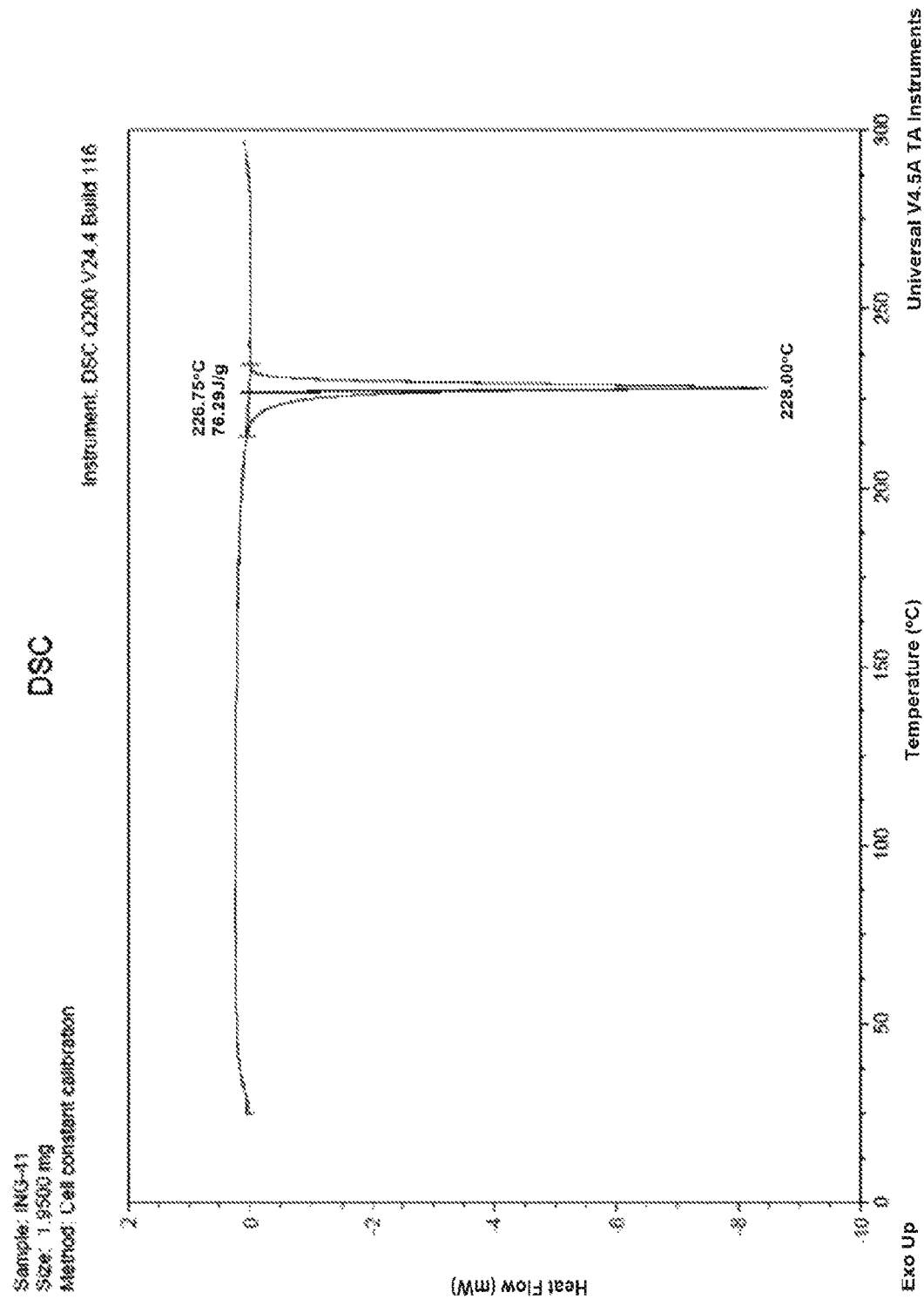
FIG. 2 shows a differential scanning calorimetry (DSC) profile of Form I of 9-ING-41.

Crystalline Form I of 9-ING-41 can be characterized by a DSC thermogram substantially as shown in FIG. 2. As FIG. 2 shows, crystalline Form I of 9-ING-41 produced an endothermic peak at 228.00° C., with a peak onset temperature of 226.75° C., and an enthalpy of melting of 76.29 J/g, when heated at a rate of 10° C./min. In some embodiments of the present disclosure, crystalline Form I of 9-ING-41 is characterized by a DSC thermogram comprising an endothermic peak at about 228° C. In other embodiments of the present disclosure, crystalline Form I of 9-ING-41 is characterized by a DSC enthalpy of melting of about 76 J/g.

Figure 3:
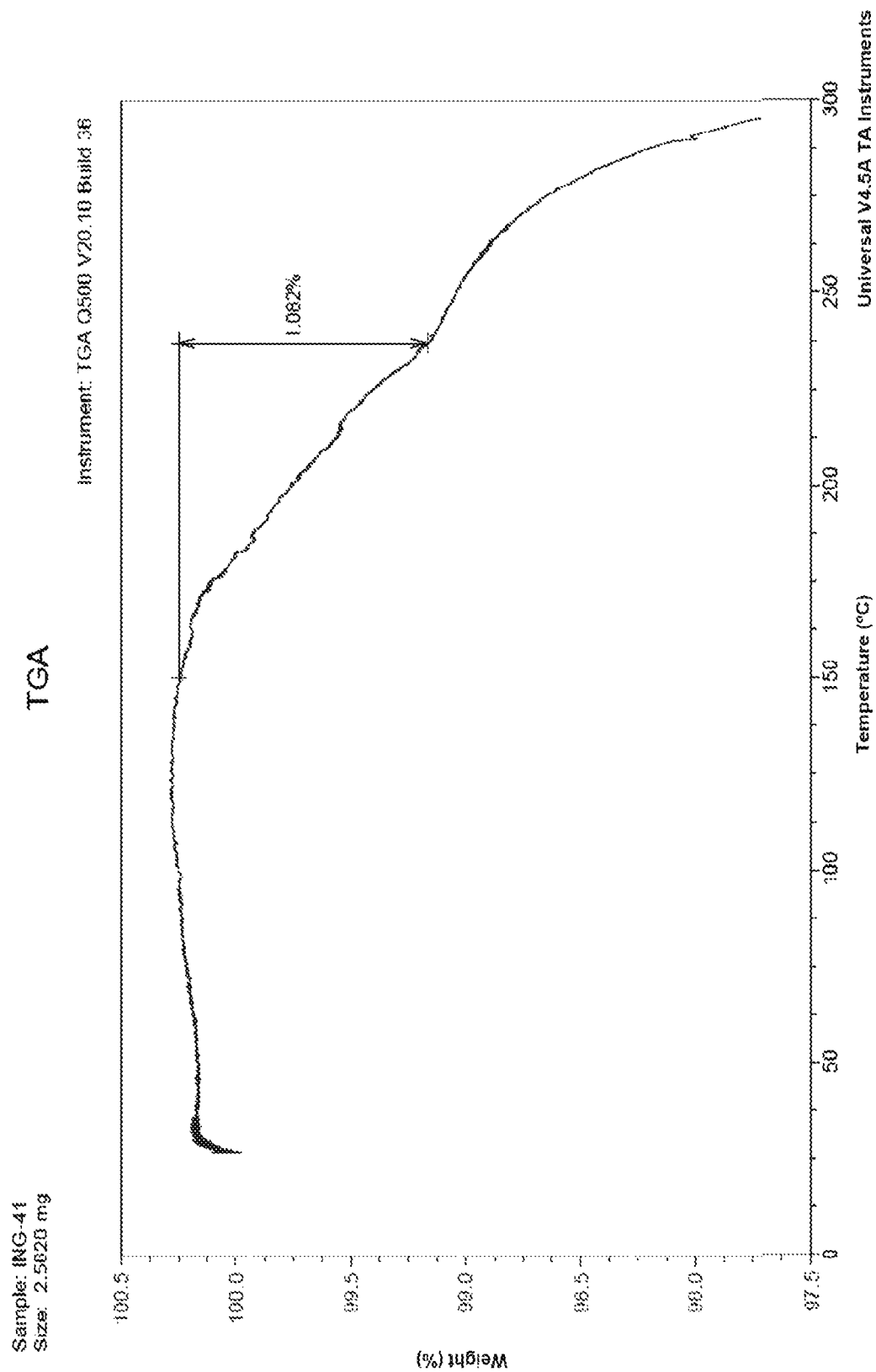
FIG. 3 shows a thermogravimetric analysis (TGA) profile of Form I of 9-ING-41.

Crystalline Form I of 9-ING-41 can be characterized by a TGA profile substantially as shown in FIG. 3 when heated at a rate of 10° C./min. As FIG. 3 shows, crystalline Form I of 9-ING-41 lost about 1% of its weight upon heating between about 150° C. and about 235° C. when heated at a rate of 10° C./min.

Figure 4:
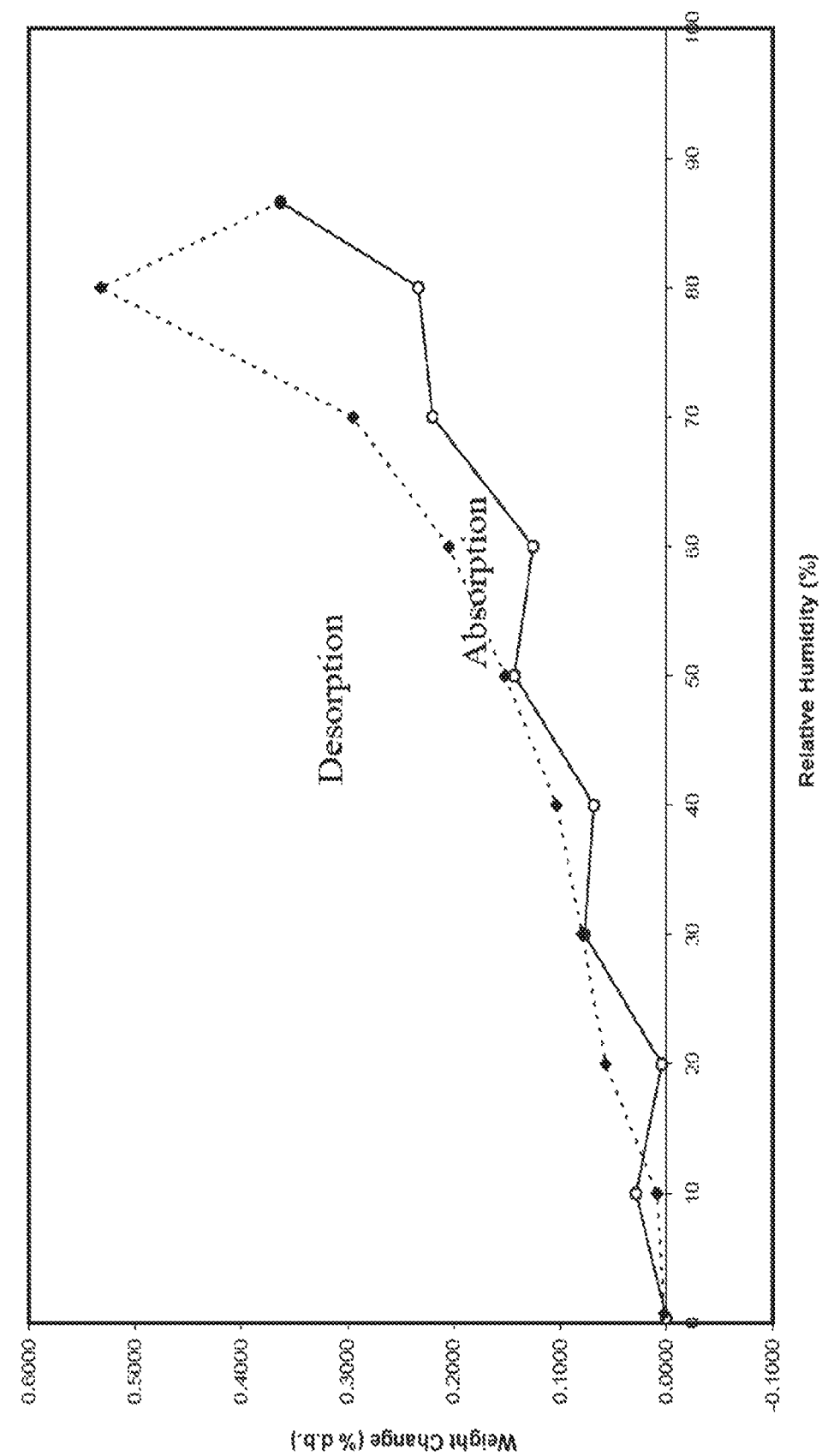
FIG. 4 shows a Dynamic Vapor Sorption ("DVS") profile for Form I of 9-ING-41.

Crystalline Form I of 9-ING-41 can be characterized by a DVS profile substantially as shown in FIG. 4. As FIG. 4 shows, crystalline Form I of 9-ING-41 gained about 0.23% by weight at 80% relative humidity.

In some embodiments of the present disclosure, crystalline Form I of 9-ING-41 is characterized by an XRPD pattern comprising peaks at 5.5, 9.4, 11.8, 13.4, 15.3, 17.7, 18.4, 18.9, 20.4, 20.8, 22.1, 24.7, and 29.3, degrees±0.2 degrees 2-theta, and a DSC thermogram comprising an endothermic peak at about 228° C. when heated at a rate of 10° C./min.

In other aspects of the present disclosure, the solid form of 9-ING-41 a solvate. In preferred aspects, the solid form of 9-ING-41 is Solvate 6. In other aspects, the solid form is 9-ING-41 Solvate 6 substantially free of any other solid form of 9-ING-41. 9-ING-41 Solvate 6 can be characterized by an XRPD substantially as shown in FIG. 5.

Figure 5:
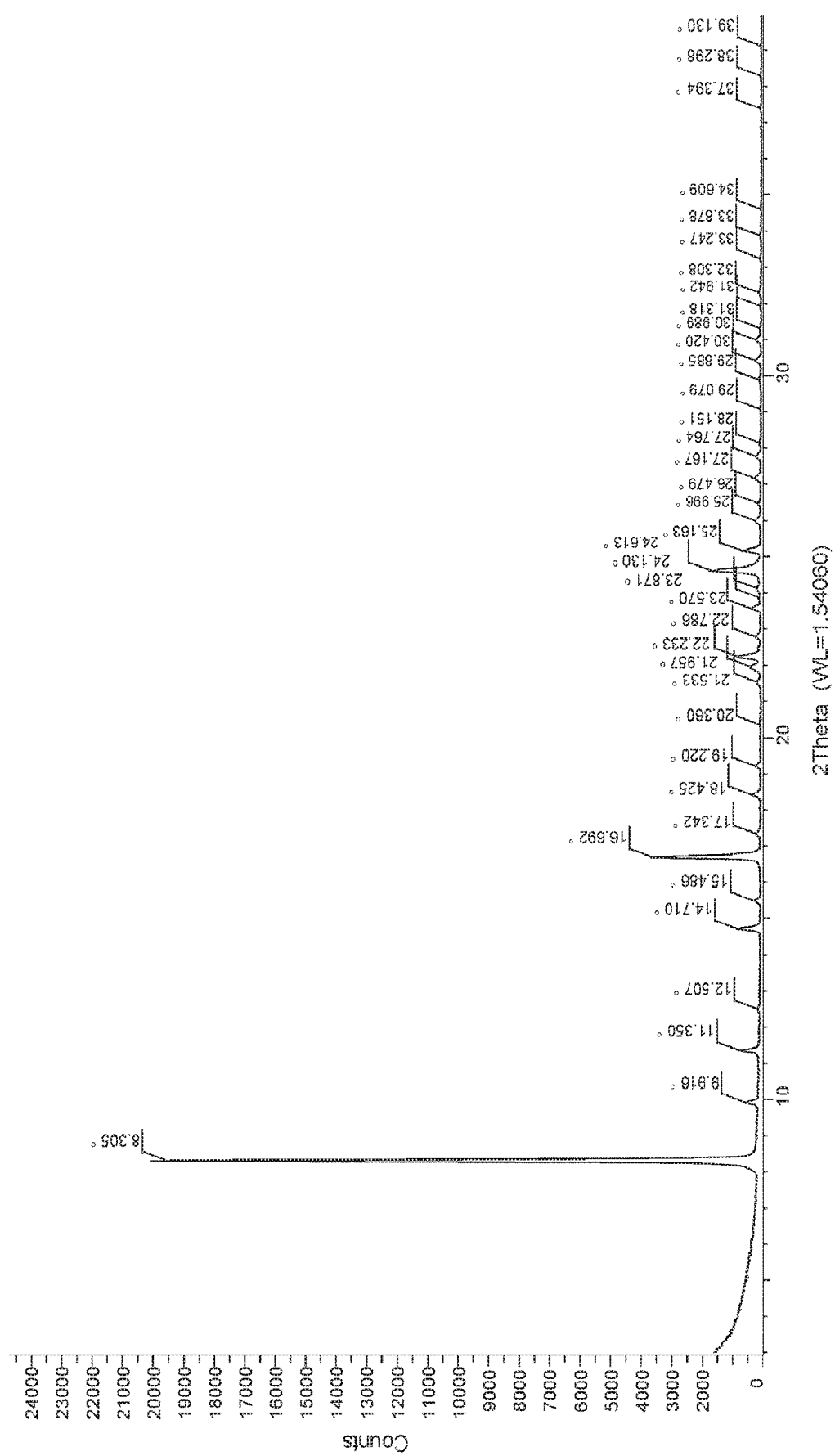
FIG. 5 shows an X-ray powder diffractogram (XRPD) of 9-ING-41 Solvate 6.

The XRPD of 9-ING-41 Solvate 6 shown in FIG. 5 comprises reflection angles (degrees 2-theta±0.2 degrees 2-theta), line spacings (d Values), and relative intensities shown in Table 2:

TABLE 2

XRPD Date for Solvate 6

| Angle (degrees 2-theta) ± 0.2 degrees 2-theta | d Value (Å) | Relative Intensity |
|---|---|---|
| 8.305 | 10.63811 | 100.0% |
| 9.916 | 8.91255 | 2.2% |
| 11.350 | 7.78956 | 3.1% |
| 12.507 | 7.07151 | 0.3% |
| 14.710 | 6.01731 | 3.7% |
| 15.486 | 5.71749 | 1.1% |
| 16.692 | 5.30693 | 18.2% |
| 17.342 | 5.10937 | 0.6% |
| 18.425 | 4.81139 | 1.5% |
| 19.220 | 4.61413 | 0.9% |
| 20.360 | 4.35829 | 0.2% |
| 21.533 | 4.12347 | 0.5% |
| 21.957 | 4.04491 | 1.6% |
| 22.233 | 3.99520 | 3.7% |
| 22.786 | 3.89955 | 0.8% |
| 23.570 | 3.77161 | 1.6% |
| 23.871 | 3.72463 | 0.1% |
| 24.130 | 3.68525 | 0.4% |
| 24.613 | 3.61398 | 8.2% |
| 25.163 | 3.53632 | 2.9% |
| 25.996 | 3.42482 | 0.8% |
| 26.479 | 3.36346 | 0.3% |
| 27.167 | 3.27980 | 1.0% |
| 27.764 | 3.21065 | 0.7% |
| 28.151 | 3.16739 | 0.2% |
| 29.079 | 3.06829 | 0.1% |
| 29.885 | 2.98741 | 0.3% |
| 30.420 | 2.93602 | 0.8% |
| 30.989 | 2.88344 | 0.7% |
| 31.318 | 2.85389 | 0.1% |
| 31.942 | 2.79951 | 0.1% |
| 32.308 | 2.76869 | 0.3% |
| 33.247 | 2.69257 | 0.2% |
| 33.878 | 2.64385 | 0.3% |
| 34.609 | 2.58964 | 0.2% |
| 37.394 | 2.40295 | 0.2% |
| 38.298 | 2.34830 | 0.2% |
| 39.130 | 2.30026 | 0.1% |

In some embodiments of the present disclosure, 9-ING-41 Solvate 6 is characterized by an XRPD pattern comprising a peak at one of the angles listed in Table 2 above).

In some embodiments, 9-ING-41 Solvate 6 is characterized by an XRPD pattern comprising a peak at 8.3 degrees±0.2 degrees 2-theta. In other embodiments, 9-ING-41 Solvate 6 is characterized by an XRPD pattern comprising one, two, three, four, or five peaks selected from 8.3, 14.7, 16.7, 22.2, and 24.6 degrees±0.2 degrees 2-theta.

Figure 6:
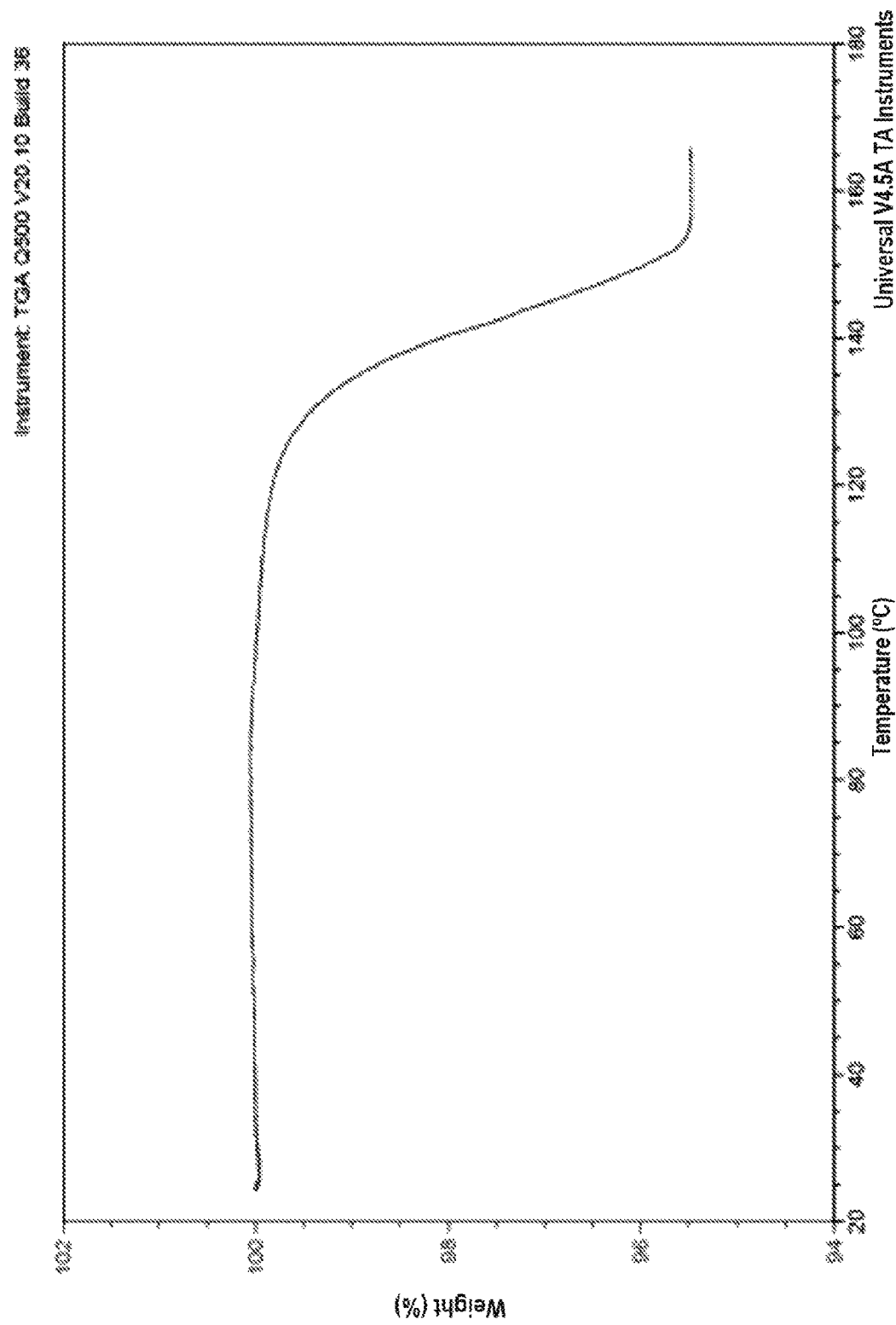
FIG. 6 shows a thermogravimetric analysis (TGA) profile of 9-ING-41 Solvate 6.

9-ING-41 Solvate 6 can be characterized by a TGA profile substantially as shown in FIG. 6. As FIG. 6 shows, Solvate 6 lost approximately 4.5% by weight upon heating between 120° C. to 150° C. when heated at a rate of 10° C./min.

In other aspects of the present disclosure, the solid form is 9-ING-41 Solvate 7. In other aspects, the solid form is 9-ING-41 Solvate 7 substantially free of any other solid form of 9-ING-41. 9-ING-41 Solvate 7 can be characterized by the XRPD substantially as shown in FIG. 7.

Figure 7:
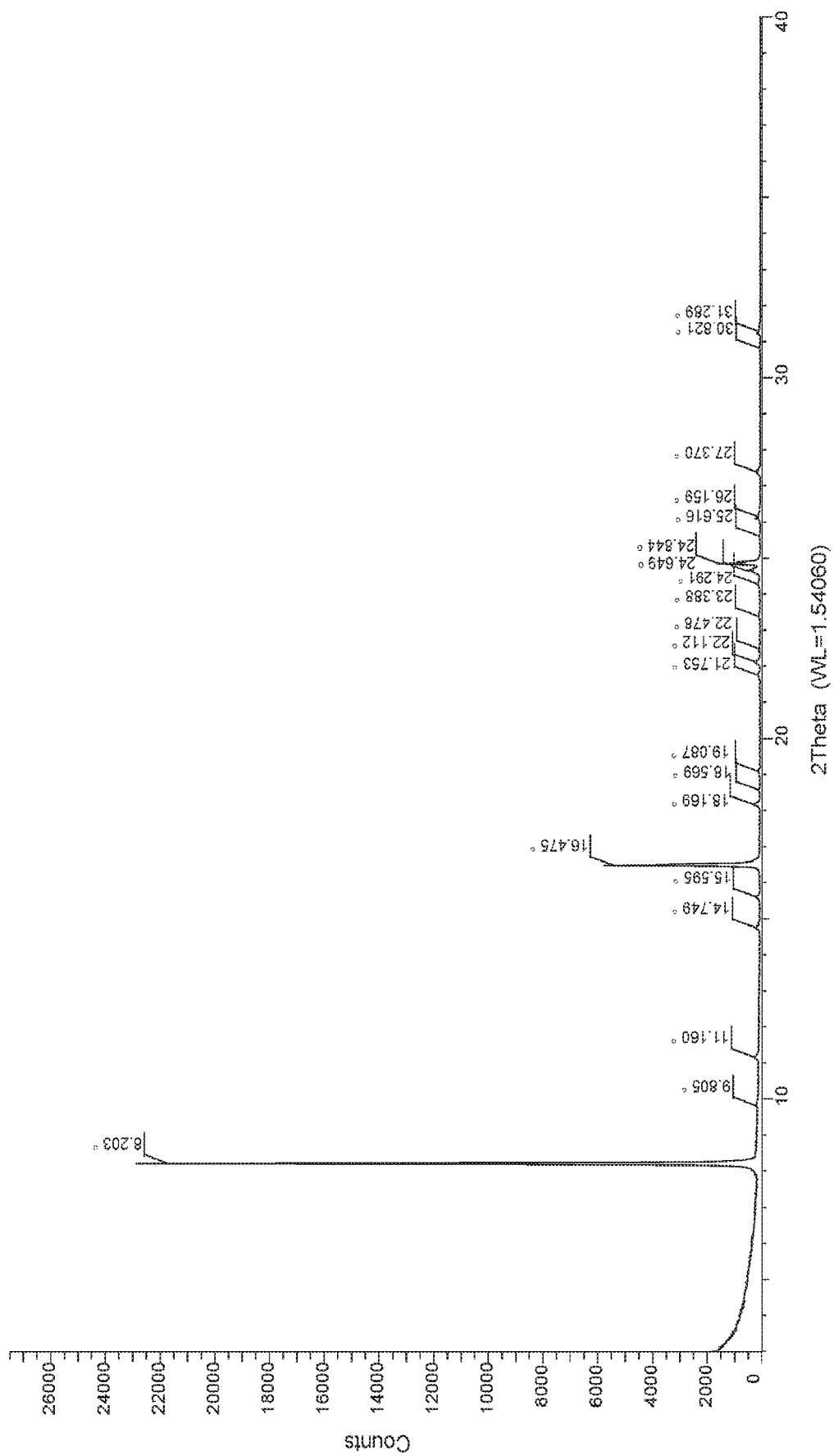
FIG. 7 shows an X-ray powder diffractogram (XRPD) of 9-ING-41 Solvate 7.

The XRPD of 9-ING-41 Solvate 7 shown in FIG. 7 comprises reflection angles (degrees 2-theta±0.2 degrees 2-theta), line spacings (d Values), and relative intensities shown in Table 3:

TABLE 3

XRPD Data for Solvate 7

| Angle (degrees 2-theta ± 0.2 degrees 2-theta) | d Value (Å) | Relative Intensity |
|---|---|---|
| 8.203 | 10.77038 | 100.0% |
| 9.805 | 9.01312 | 0.2% |
| 11.160 | 7.92223 | 0.6% |
| 14.749 | 6.00130 | 0.7% |
| 15.595 | 5.67774 | 0.5% |
| 16.475 | 5.37619 | 24.7% |
| 18.169 | 4.87864 | 1.0% |
| 18.569 | 4.77460 | 0.1% |
| 19.087 | 4.64603 | 0.2% |
| 21.753 | 4.08233 | 0.3% |
| 22.112 | 4.01691 | 0.7% |
| 22.478 | 3.95231 | 0.0% |
| 23.388 | 3.80053 | 0.3% |
| 24.291 | 3.66119 | 0.5% |
| 24.649 | 3.60891 | 2.2% |
| 24.844 | 3.58089 | 6.9% |
| 25.616 | 3.47472 | 0.1% |
| 26.159 | 3.40390 | 0.4% |
| 27.370 | 3.25590 | 0.4% |
| 30.821 | 2.89875 | 0.2% |
| 31.289 | 2.85649 | 0.3% |

In some embodiments of the present disclosure, 9-ING-41 Solvate 7 is characterized by an XRPD pattern comprising a peak at one of the angles listed in Table 3 above.

In some embodiments, 9-ING-41 Solvate 7 is characterized by an XRPD pattern comprising a peak at 8.2 degrees±0.2 degrees 2-theta. In other embodiments, 9-ING-41 Solvate 6 is characterized by an XRPD pattern comprising one, two, three, or four peaks selected from 8.2, 16.5, 24.6, and 24.8 degrees±0.2 degrees 2-theta.

Figure 8:
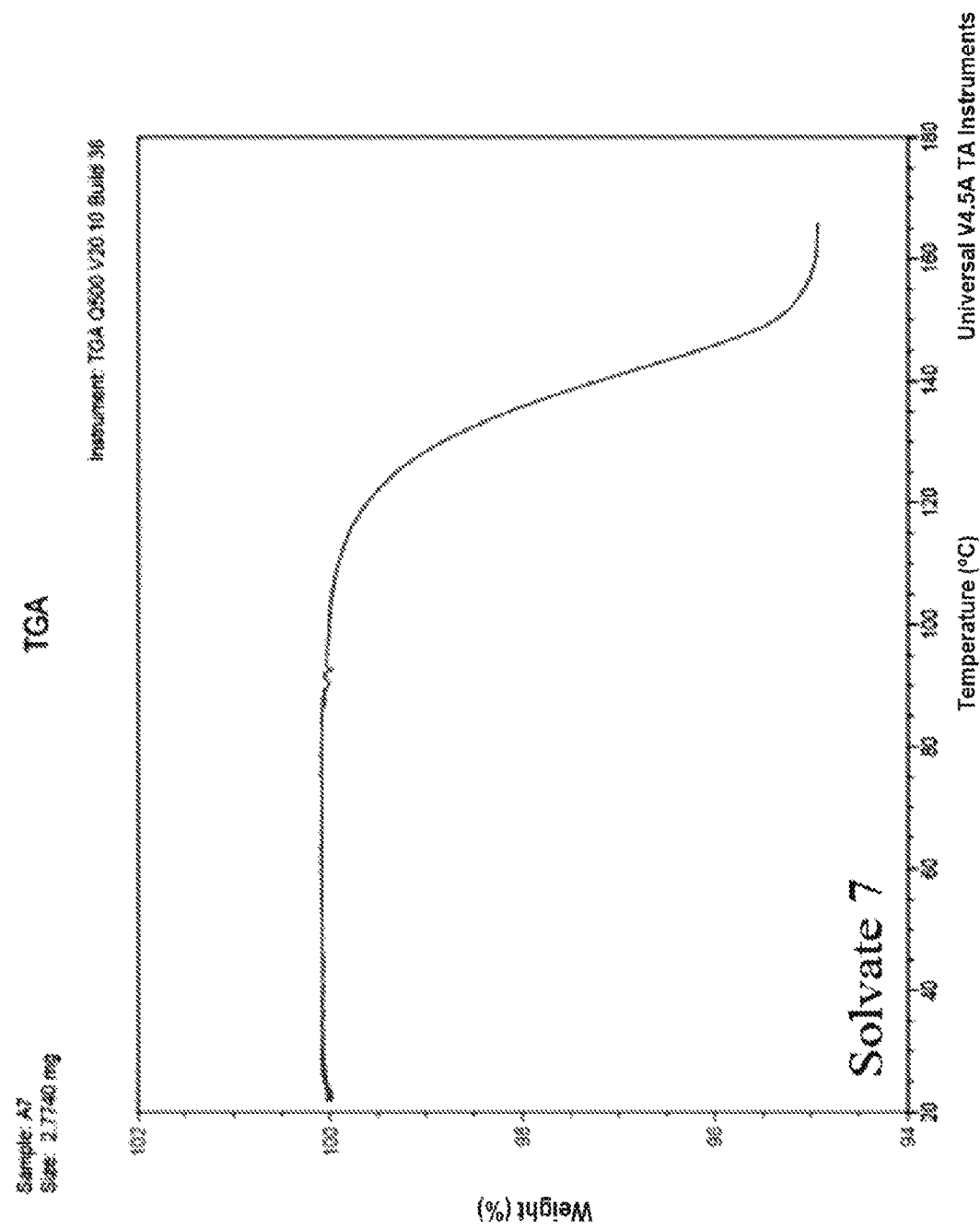
FIG. 8 shows a thermogravimetric analysis (TGA) profile of 9-ING-41 Solvate 7.

9-ING-41 Solvate 7 can be characterized by a TGA profile substantially as shown in FIG. 8 when heated at a rate of 10° C./min. As FIG. 8 shows, Solvate 7 lost approximately 5% by weight upon heating between 100° C. and 160° C. when heated at a rate of 10° C./min.

In other aspects of the present disclosure, the solid form of 9-ING-41 is 9-ING-41 Solvate 8. In other aspects, the solid form is 9-ING-41 Solvate 8 substantially free of any other solid form of 9-ING-41. 9-ING-41 Solvate 8 can be characterized by an XRPD substantially as shown in FIG. 9.

Figure 9:
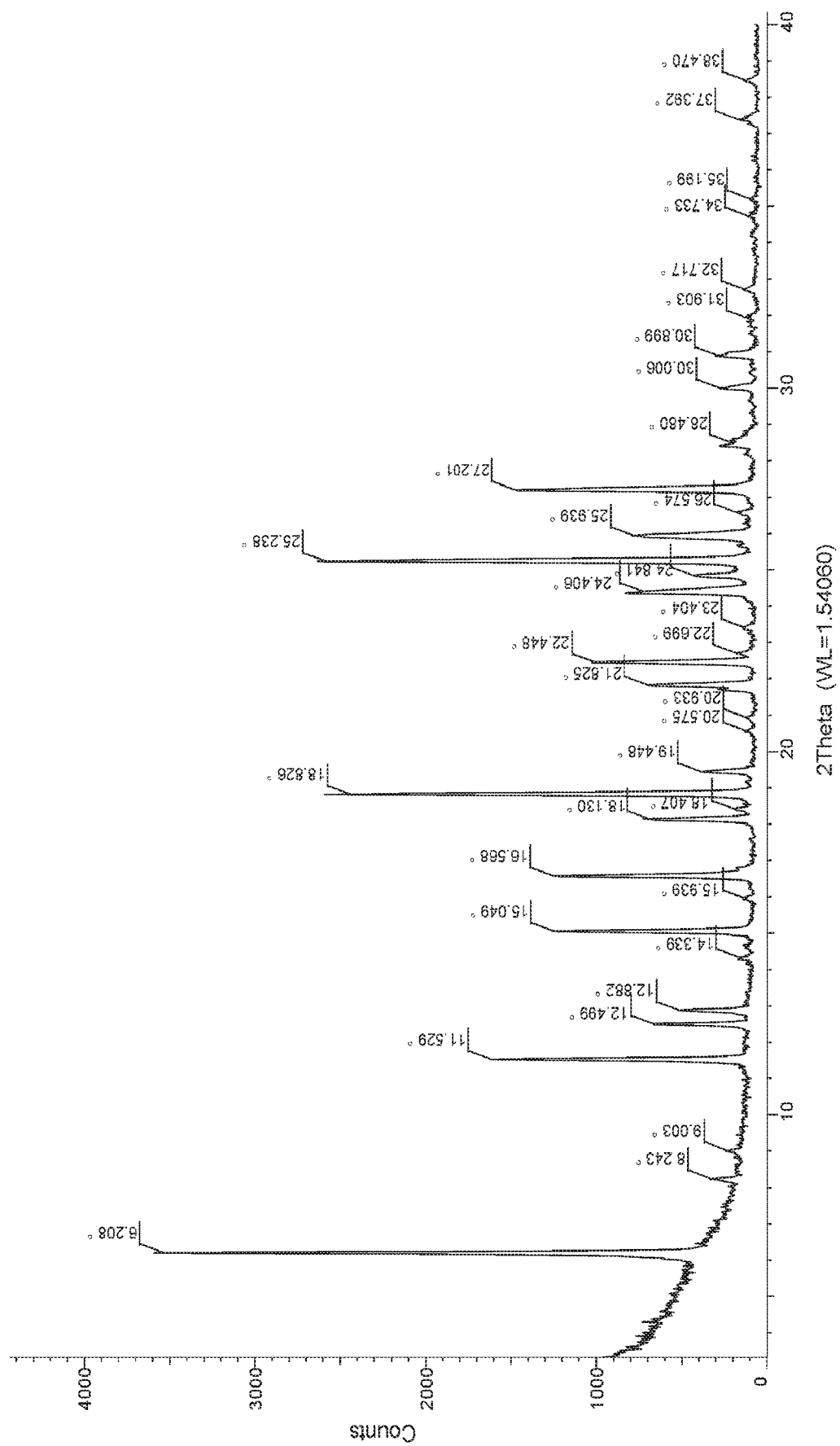
FIG. 9 shows an X-ray powder diffractogram (XRPD) of 9-ING-41 Solvate 8.

The XRPD of 9-ING-41 Solvate 8 shown in FIG. 9 comprises reflection angles (degrees 2-theta±0.2 degrees 2-theta), line spacings (d Values), and relative intensities shown in Table 4:

TABLE 4

XRPD Data for Solvate 8

| Angle (degrees 2-theta ± 0.2 degrees 2-theta) | d Value (Å) | Relative Intensity |
|---|---|---|
| 6.208 | 14.22674 | 100.0% |
| 8.243 | 10.71793 | 4.6% |
| 9.003 | 9.81441 | 2.5% |
| 11.529 | 7.66953 | 47.7% |
| 12.499 | 7.07640 | 17.4% |
| 12.882 | 6.86687 | 12.8% |
| 14.339 | 6.17192 | 2.1% |
| 15.049 | 5.88248 | 36.7% |
| 15.939 | 5.55574 | 1.2% |
| 16.568 | 5.34634 | 37.0% |
| 18.130 | 4.88916 | 19.1% |
| 18.407 | 4.81608 | 3.2% |
| 18.826 | 4.70985 | 74.8% |

TABLE 4-continued

XRPD Data for Solvate 8

| Angle (degrees 2-theta ± 0.2 degrees 2-theta) | d Value (Å) | Relative Intensity |
|---|---|---|
| 19.448 | 4.56070 | 9.7% |
| 20.575 | 4.31325 | 1.5% |
| 20.933 | 4.24036 | 1.4% |
| 21.825 | 4.06900 | 19.8% |
| 22.448 | 3.95741 | 29.3% |
| 22.699 | 3.91418 | 3.1% |
| 23.404 | 3.79793 | 1.7% |
| 24.406 | 3.64422 | 20.4% |
| 24.841 | 3.58131 | 10.7% |
| 25.238 | 3.52590 | 79.1% |
| 25.939 | 3.43227 | 21.7% |
| 26.574 | 3.35162 | 2.6% |
| 27.201 | 3.27574 | 44.0% |
| 28.480 | 3.13151 | 3.8% |
| 30.006 | 2.97567 | 6.5% |
| 30.899 | 2.89167 | 6.8% |
| 31.903 | 2.80289 | 1.1% |
| 32.717 | 2.73495 | 2.1% |
| 34.733 | 2.58073 | 1.6% |
| 35.199 | 2.54762 | 1.2% |
| 37.392 | 2.40307 | 3.4% |
| 38.470 | 2.33820 | 2.3% |

In some embodiments of the present disclosure, 9-ING-41 Solvate 8 is characterized by an XRPD pattern comprising a peak at one of the angles listed in Table 4 above.

In some embodiments, 9-ING-41 Solvate 8 is characterized by an XRPD pattern comprising a peak at 6.2 degrees±0.2 degrees 2-theta. In other embodiments, 9-ING-41 Solvate 8 is characterized by an XRPD pattern comprising one, two, three, four, five, six, seven, eight, nine, or ten peaks selected from 6.2, 11.5, 12.5, 12.9, 15.0, 16.6, 18.8, 21.8, 25.2, and 27.2±0.2 degrees 2-theta.

Figure 10:
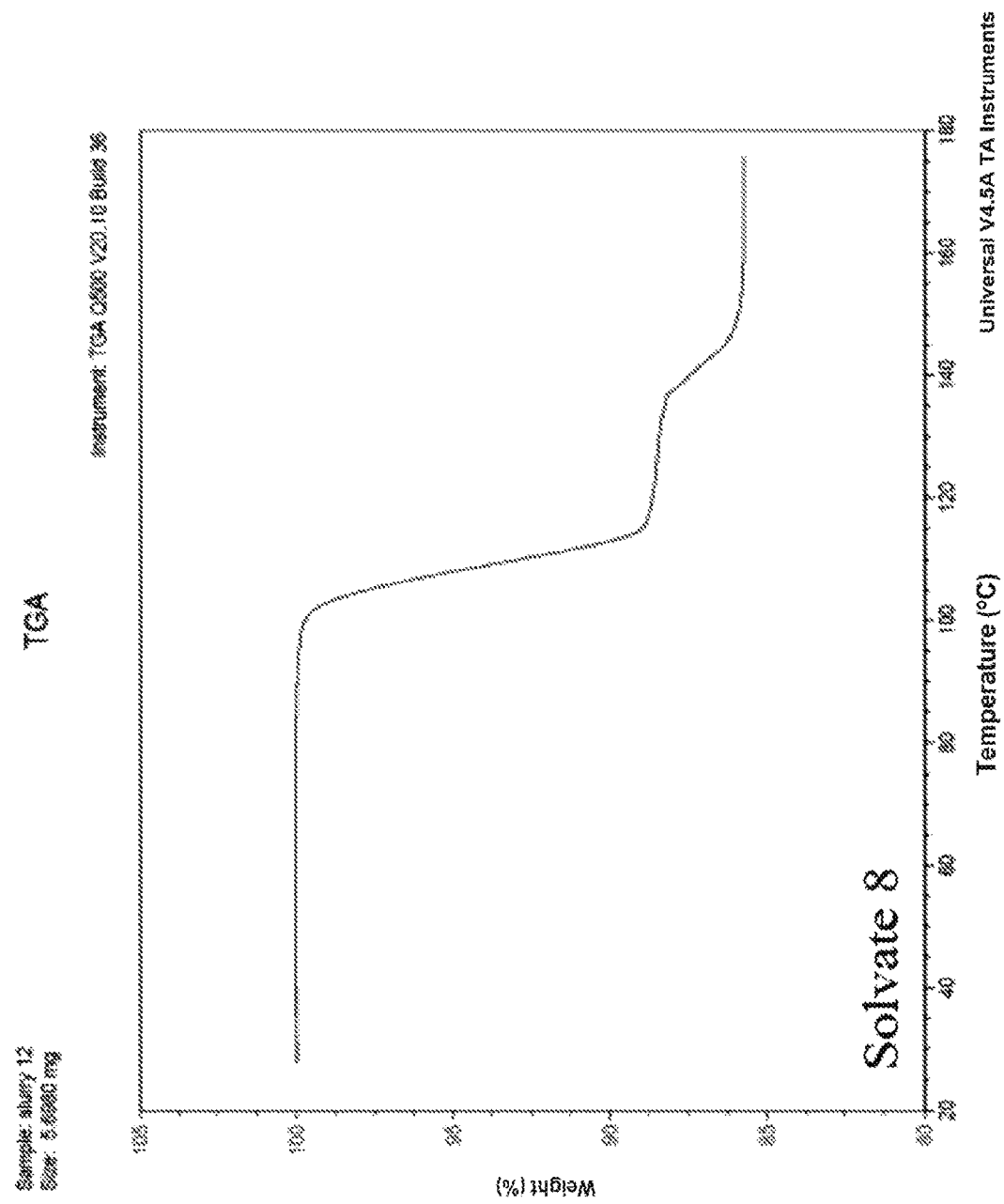
FIG. 10 shows a thermogravimetric analysis (TGA) profile of 9-ING-41 Solvate 8.

9-ING-41 Solvate 8 can be characterized by a TGA profile substantially as shown in FIG. 10. As FIG. 10 shows, Solvate 8 lost approximately 11.25% by weight upon heating between 90° C. and 120° C., and then lost an additional 2.5% by weight between 130° C. and 150° C. when heated at a rate of 10° C./min.

Figure 11:
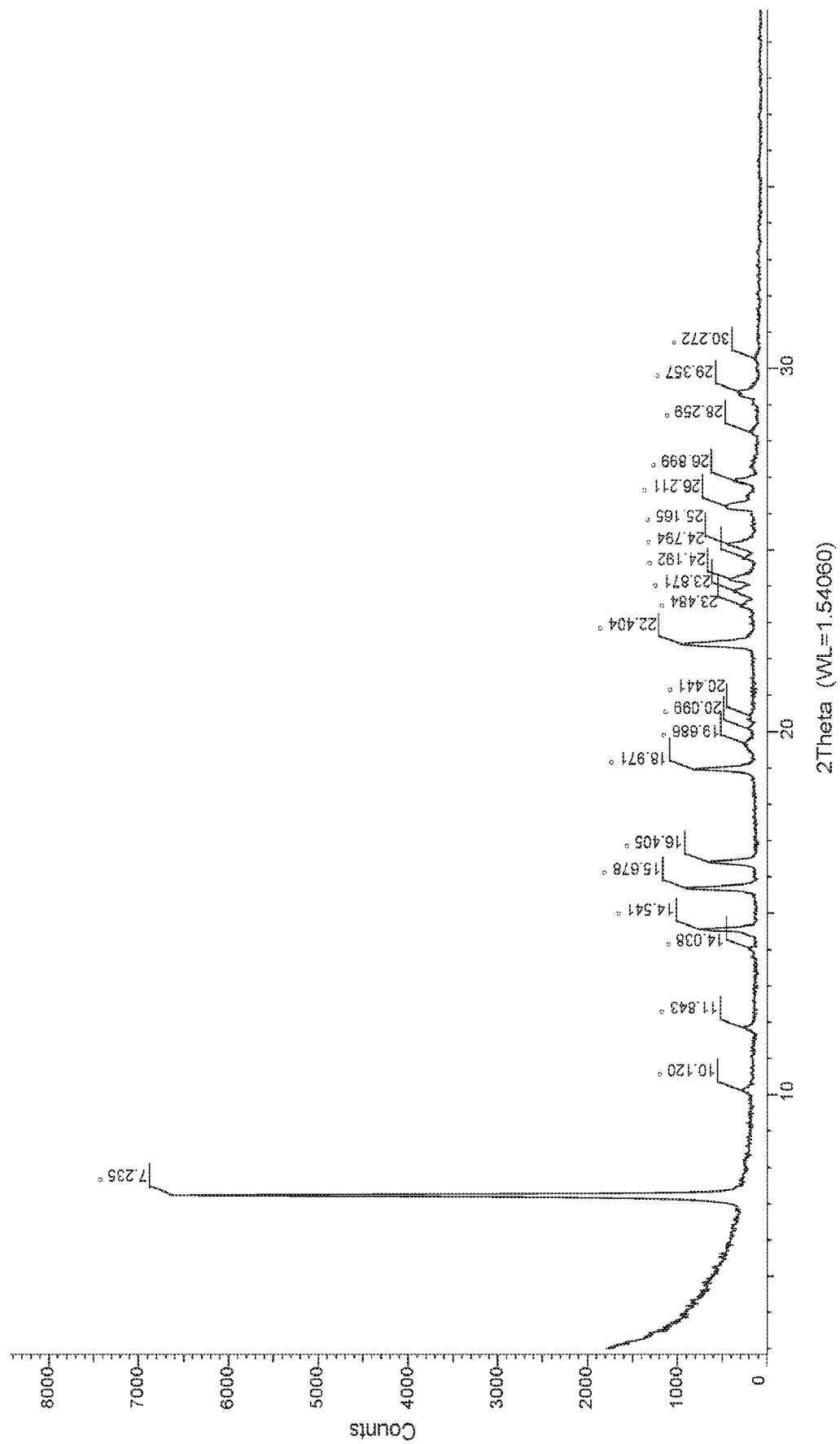
FIG. 11 shows an X-ray powder diffractogram (XRPD) of 9-ING-41 Solvate 9.

In other aspects of the present disclosure, the solid form of 9-ING-41 is 9-ING-41 Solvate 9. In other aspects, the solid form is 9-ING-41 Solvate 9 substantially free of any other solid form of 9-ING-41. 9-ING-41 Solvate 9 can be characterized by an XRPD substantially as shown in FIG. 11.

The XRPD of 9-ING-41 Solvate 9 shown in FIG. 11 comprises reflection angles (degrees 2-theta±0.2 degrees 2-theta), line spacings (d Values), and relative intensities shown in Table 5 below:

TABLE 5

XRPD Data for Solvate 9

| Angle (degrees 2-theta ± 0.2 degrees 2-theta) | d Value (Å) | Relative Intensity |
|---|---|---|
| 7.235 | 12.20810 | 100.0% |
| 10.120 | 8.73340 | 1.9% |
| 11.843 | 7.46678 | 1.9% |
| 14.038 | 6.30387 | 1.0% |
| 14.541 | 6.08681 | 9.8% |
| 15.678 | 5.64765 | 12.1% |
| 16.405 | 5.39902 | 8.3% |
| 18.971 | 4.67421 | 10.6% |

TABLE 5-continued

XRPD Data for Solvate 9

| Angle (degrees 2-theta ± 0.2 degrees 2-theta) | d Value (Å) | Relative Intensity |
|---|---|---|
| 19.686 | 4.50594 | 1.5% |
| 20.099 | 4.41431 | 1.0% |
| 20.441 | 4.34123 | 0.5% |
| 22.404 | 3.96516 | 12.5% |
| 23.484 | 3.78519 | 1.9% |
| 23.871 | 3.72462 | 3.0% |
| 24.192 | 3.67590 | 3.8% |
| 24.794 | 3.58802 | 1.5% |
| 25.165 | 3.53604 | 4.3% |
| 26.211 | 3.39727 | 4.9% |
| 26.899 | 3.31189 | 3.6% |
| 28.259 | 3.15550 | 1.5% |
| 29.357 | 3.03992 | 3.2% |
| 30.272 | 2.95011 | 0.5% |

In some embodiments of the present disclosure, 9-ING-41 Solvate 9 is characterized by an XRPD pattern comprising a peak at one of the angles listed in Table 5 above).

In some embodiments, 9-ING-41 Solvate 9 is characterized by an XRPD pattern comprising a peak at 7.2 degrees±0.2 degrees 2-theta. In other embodiments, 9-ING-41 Solvate 9 is characterized by an XRPD pattern comprising one, two, three, four, five, six, or peaks selected from 7.2, 14.5, 15.7, 19.0, 22.4, 25.2, and 26.2±0.2 degrees 2-theta.

Figure 12:
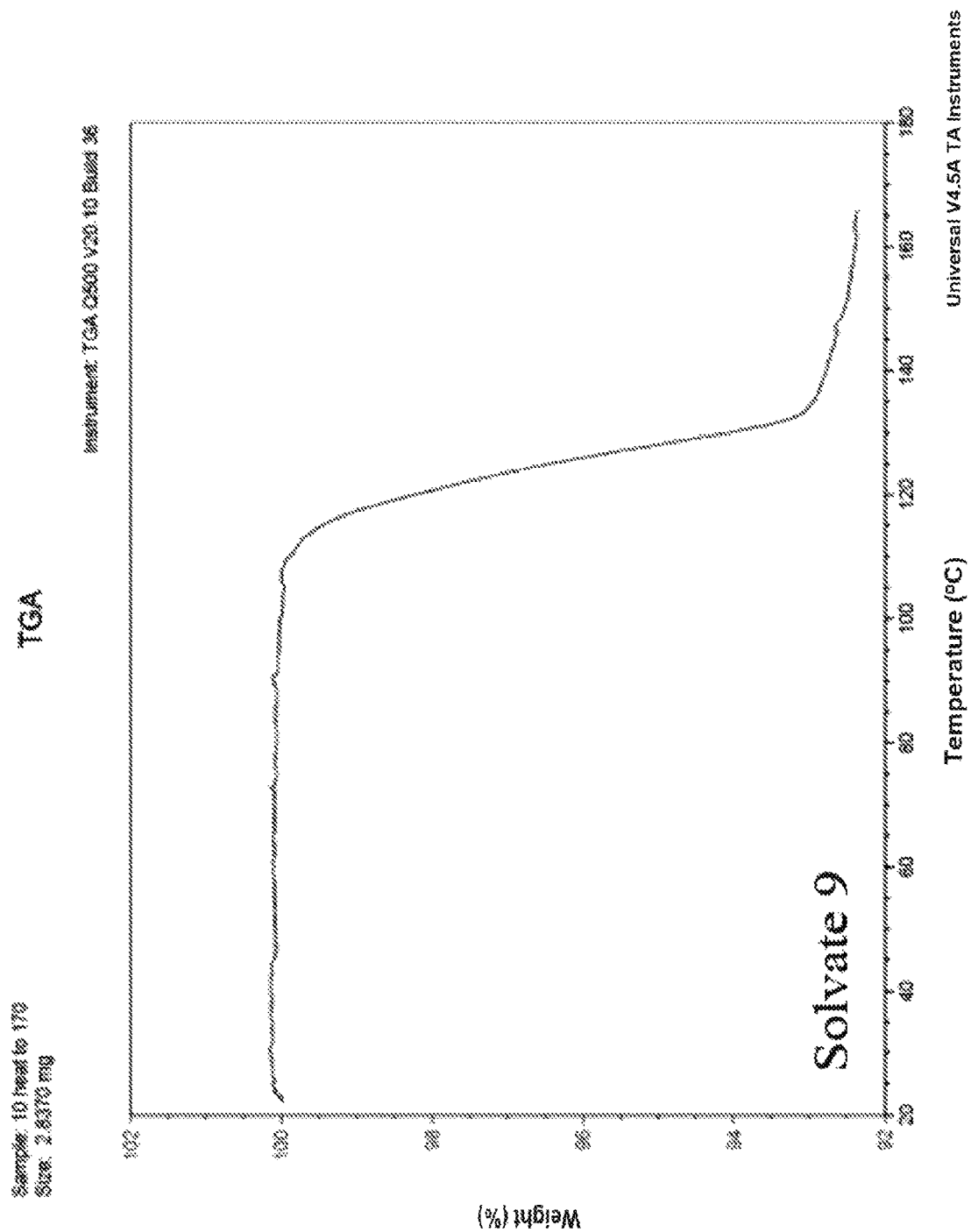
FIG. 12 shows a thermogravimetric analysis (TGA) profile of 9-ING-41 Solvate 9.

9-ING-41 Solvate 9 can be characterized by a TGA profile substantially as shown in FIG. 12 when heated at a rate of 10° C./min. As FIG. 12 shows, Solvate 9 lost approximately 7.5% by weight upon heating between 100° C. and 160° C. when heated at a rate of 10° C./min.

In other aspects of the present disclosure, the solid form of 9-ING-41 is 9-ING-41 Solvate 3. In other aspects, the solid form is 9-ING-41 Solvate 3 substantially free of any other solid form of 9-ING-41. 9-ING-41 Solvate 3 can be characterized by an XRPD substantially as shown in FIG. 13.

Figure 13:
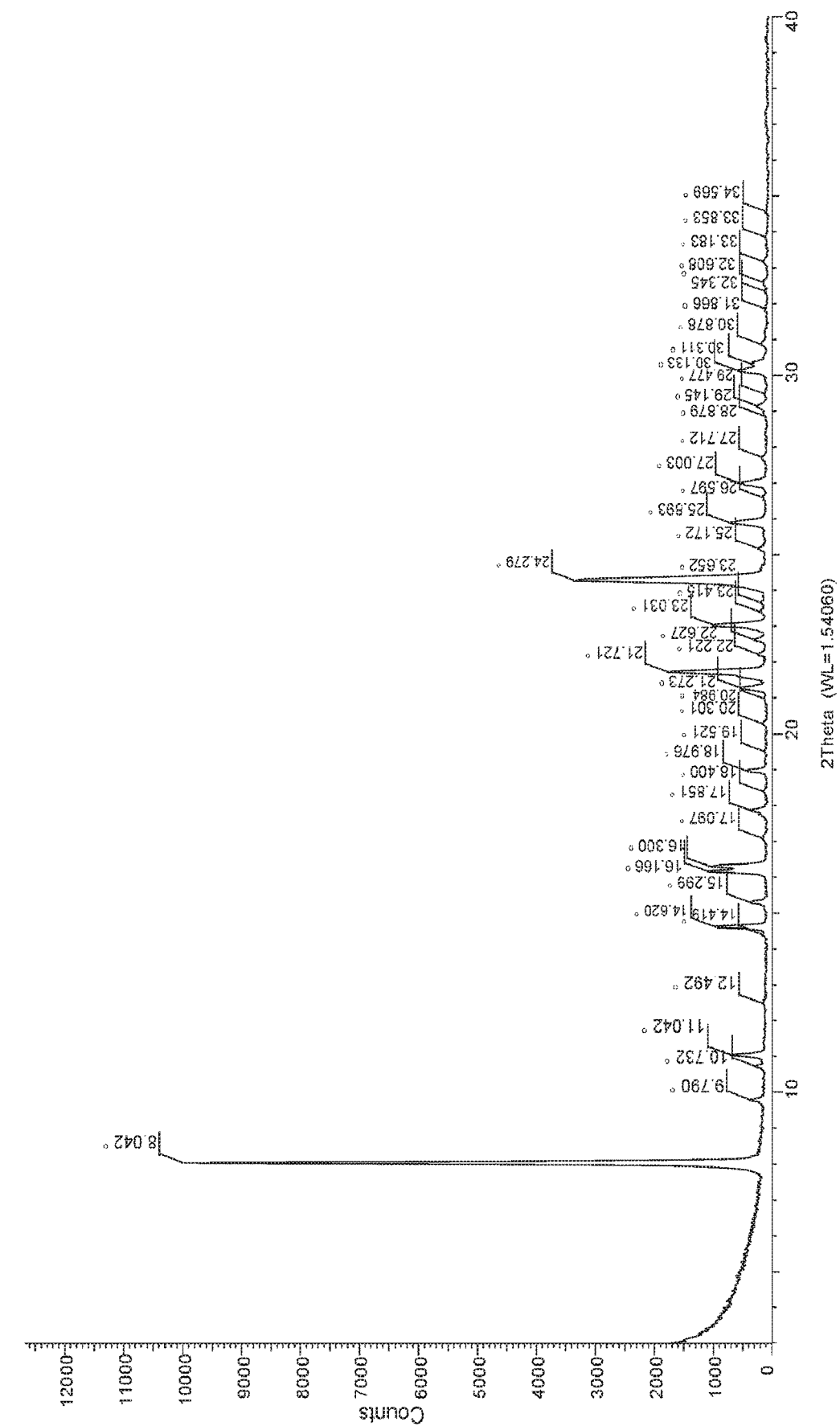
FIG. 13 shows an X-ray powder diffractogram (XRPD) of 9-ING-41 Solvate 3.

The XRPD of 9-ING-41 Solvate 3 shown in FIG. 13 comprises reflection angles (degrees 2-theta±0.2 degrees 2-theta), line spacings (d Values), and relative intensities shown in Table 6:

TABLE 6

XRPD Data for Solvate 3

| Angle (degrees 2-theta ± 0.2 degrees 2-theta) | d Value (Å) | Relative Intensity |
|---|---|---|
| 8.042 | 10.98464 | 100.0% |
| 9.790 | 9.02769 | 2.3% |
| 10.732 | 8.23722 | 1.5% |
| 11.042 | 8.00621 | 5.8% |
| 12.492 | 7.08006 | 0.6% |
| 14.419 | 6.13794 | 0.8% |
| 14.620 | 6.05420 | 9.0% |
| 15.299 | 5.78669 | 2.9% |
| 16.166 | 5.47837 | 10.1% |
| 16.300 | 5.43373 | 9.7% |
| 17.097 | 5.18200 | 0.8% |
| 17.851 | 4.96496 | 2.5% |
| 18.400 | 4.81788 | 0.6% |
| 18.976 | 4.67296 | 3.5% |
| 19.521 | 4.54378 | 0.3% |
| 20.301 | 4.37095 | 0.8% |
| 20.984 | 4.23009 | 0.5% |
| 21.273 | 4.17339 | 4.3% |

TABLE 6-continued

XRPD Data for Solvate 3

| Angle (degrees 2-theta ± 0.2 degrees 2-theta) | d Value (Å) | Relative Intensity |
|---|---|---|
| 21.721 | 4.08828 | 16.8% |
| 22.221 | 3.99739 | 1.2% |
| 22.627 | 3.92661 | 1.7% |
| 23.031 | 3.85859 | 8.7% |
| 23.415 | 3.79622 | 0.9% |
| 23.652 | 3.75862 | 0.4% |
| 24.279 | 3.66306 | 32.6% |
| 25.172 | 3.53505 | 1.1% |
| 25.893 | 3.43825 | 6.1% |
| 26.597 | 3.34881 | 0.4% |
| 27.003 | 3.29932 | 4.6% |
| 27.712 | 3.21656 | 0.7% |
| 28.879 | 3.08910 | 0.7% |
| 29.145 | 3.06149 | 1.6% |
| 29.477 | 3.02780 | 0.3% |
| 30.133 | 2.96340 | 4.9% |
| 30.311 | 2.94641 | 2.5% |
| 30.878 | 2.89351 | 0.9% |
| 31.866 | 2.80603 | 0.3% |
| 32.345 | 2.76560 | 0.4% |
| 32.608 | 2.74392 | 0.8% |
| 33.183 | 2.69761 | 0.8% |
| 33.853 | 2.64578 | 0.4% |
| 34.569 | 2.59257 | 0.3% |

In some embodiments of the present disclosure, 9-ING-41 Solvate 3 is characterized by an XRPD pattern comprising a peak at one of the angles listed in Table 6 above.

In some embodiments, 9-ING-41 Solvate 3 is characterized by an XRPD pattern comprising a peak at 8.0 degrees±0.2 degrees 2-theta). In other embodiments, 9-ING-41 Solvate 3 is characterized by an XRPD pattern comprising one, two, three, four, five, six, seven, or eight peaks selected from 8.0, 14.6, 16.2, 16.3, 21.7, 23.0, 24.3, and 25.9±0.2 degrees 2-theta.

Figure 14:
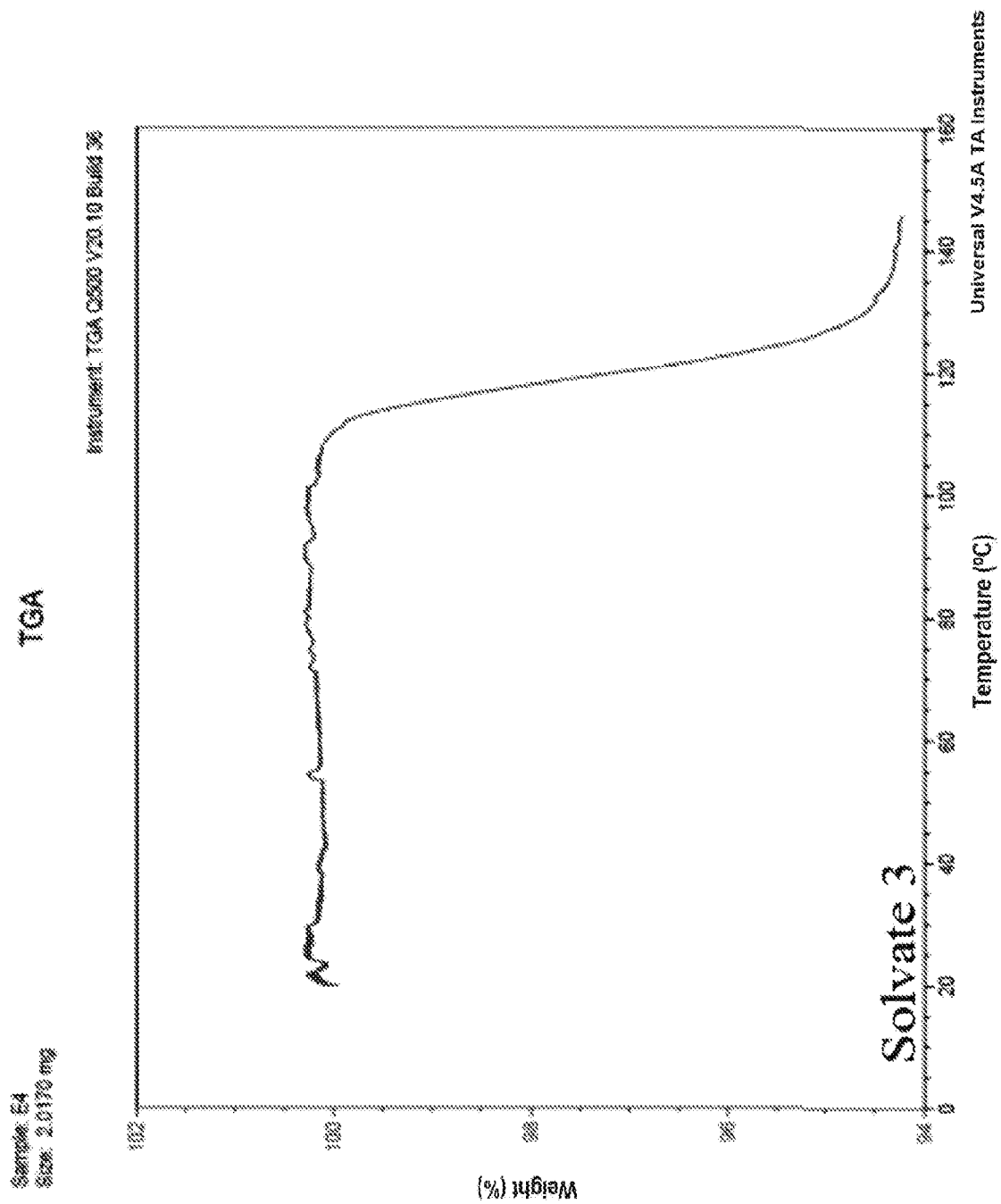
FIG. 14 shows a thermogravimetric analysis (TGA) profile of 9-ING-41 Solvate 3.

9-ING-41 Solvate 3 can be characterized by a TGA profile substantially as shown in FIG. 14 when heated at a rate of 10° C./min. As FIG. 14 shows, Solvate 3 lost approximately 5.7% by weight upon heating between 100° C. and 140° C. when heated at a rate of 10° C./min.

Figure 15:
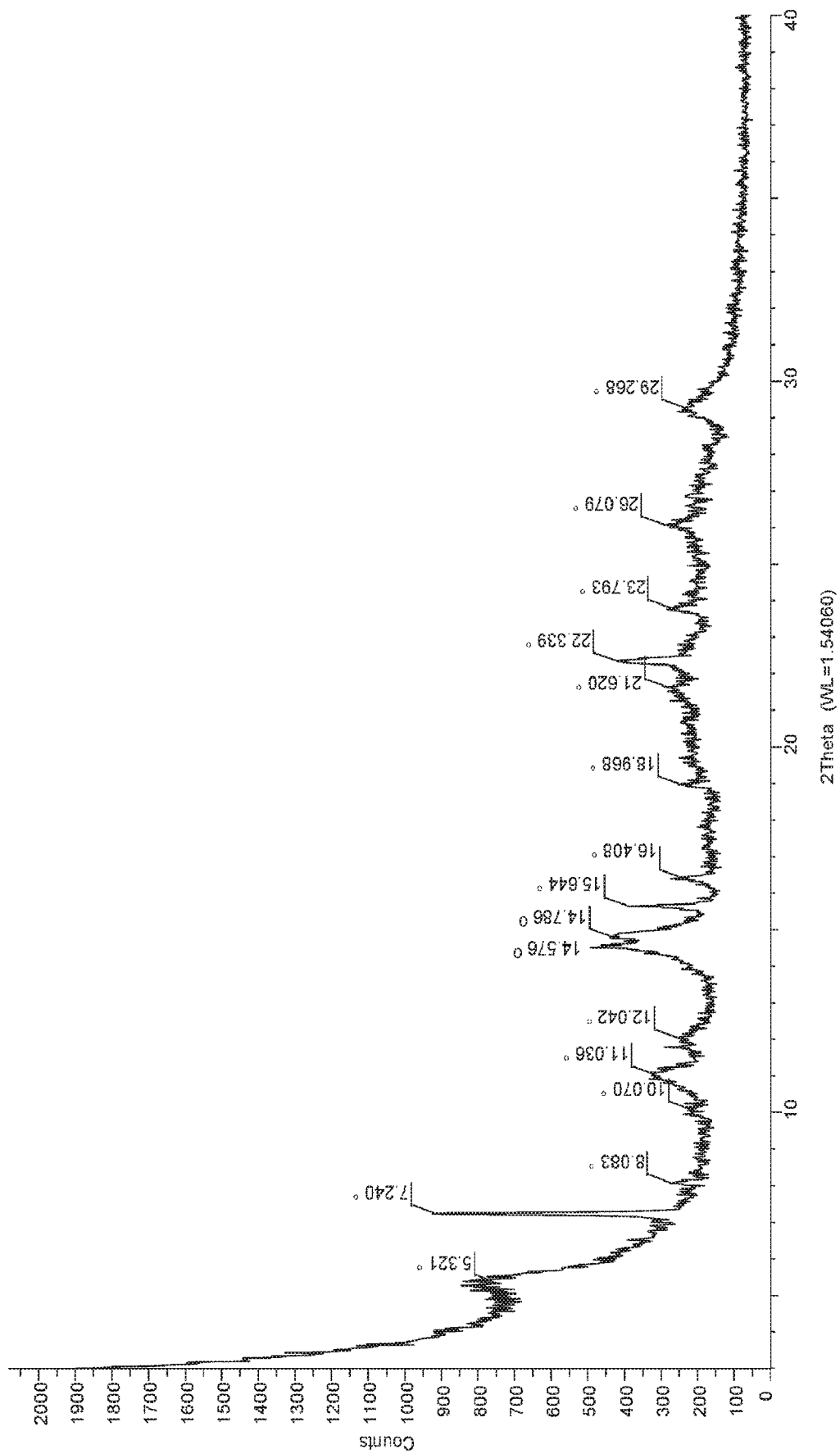
FIG. 15 shows an X-ray powder diffractogram (XRPD) of 9-ING-41 Solvate 1.

In other aspects of the present disclosure, the solid form of 9-ING-41 is 9-ING-41 Solvate 1. In other aspects, the solid form is 9-ING-41 Solvate 1 substantially free of any other solid form of 9-ING-41. 9-ING-41 Solvate 1 can be characterized by an XRPD substantially as shown in FIG. 15.

The XRPD of 9-ING-41 Solvate 1 shown in FIG. 15 comprises reflection angles (degrees 2-theta±0.2 degrees 2-theta), line spacings (d Values), and relative intensities shown in Table 7 below:

TABLE 7

XRPD Data for Solvate 1

| Angle (degrees 2-theta ± 0.2 degrees 2-theta) | d Value (Å) | Relative Intensity |
|---|---|---|
| 5.321 | 16.59363 | 25.3% |
| 7.240 | 12.20007 | 100.0% |
| 8.083 | 10.92932 | 10.9% |
| 10.070 | 8.77715 | 5.7% |
| 11.036 | 8.01089 | 20.5% |
| 12.042 | 7.34390 | 11.7% |
| 14.576 | 6.07233 | 38.9% |

TABLE 7-continued

XRPD Data for Solvate 1

| Angle (degrees 2-theta ± 0.2 degrees 2-theta) | d Value (Å) | Relative Intensity |
|---|---|---|
| 14.786 | 5.98655 | 39.8% |
| 15.644 | 5.65995 | 34.6% |
| 16.408 | 5.39826 | 11.9% |
| 18.968 | 4.67504 | 11.7% |
| 21.620 | 4.10708 | 12.2% |
| 22.339 | 3.97657 | 33.8% |
| 23.793 | 3.73663 | 12.5% |
| 26.079 | 3.41415 | 16.2% |
| 29.268 | 3.04898 | 14.6% |

In some embodiments of the present disclosure, 9-ING-41 Solvate 1 is characterized by an XRPD pattern comprising a peak at one of the angles listed in Table 7 above.

In some embodiments, 9-ING-41 Solvate 1 is characterized by an XRPD pattern comprising a peak at 7.2 degrees±0.2 degrees 2-theta. In other embodiments, 9-ING-41 Solvate 1 is characterized by an XRPD pattern comprising one, two, three, four, five, or six peaks selected from 7.2, 11.0, 14.6, 14.8, 15.6, and 22.3±0.2 degrees 2-theta.

Figure 16:
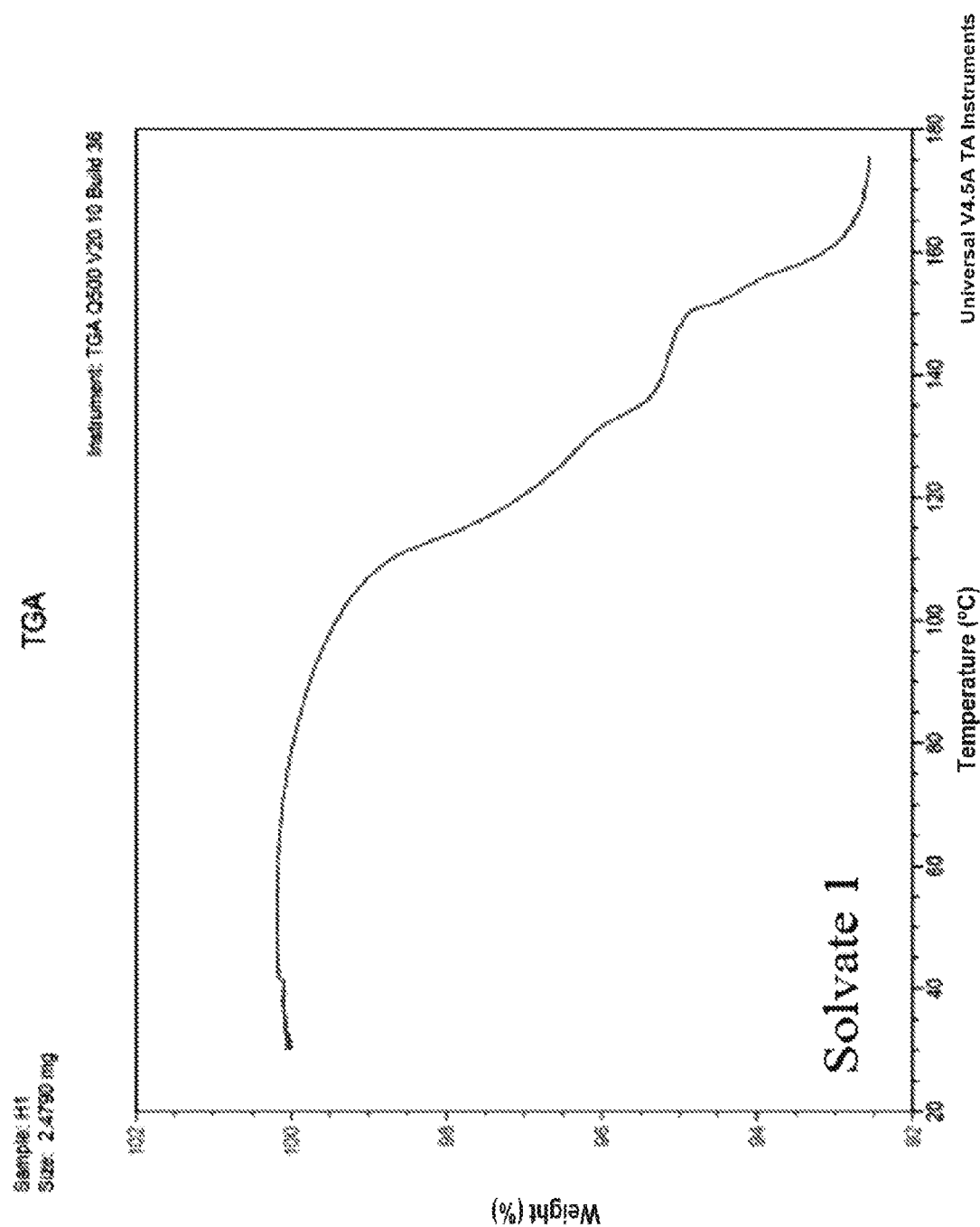
FIG. 16 shows a thermogravimetric analysis (TGA) profile of 9-ING-41 Solvate 1.

9-ING-41 Solvate 1 can be characterized by a TGA profile substantially as shown in FIG. 16 when heated at a rate of 10° C./min. As FIG. 16 shows, Solvate 1 lost approximately 7.5% by weight upon heating between 80° C. and 160° C. when heated at a rate of 10° C./min.

Figure 17:
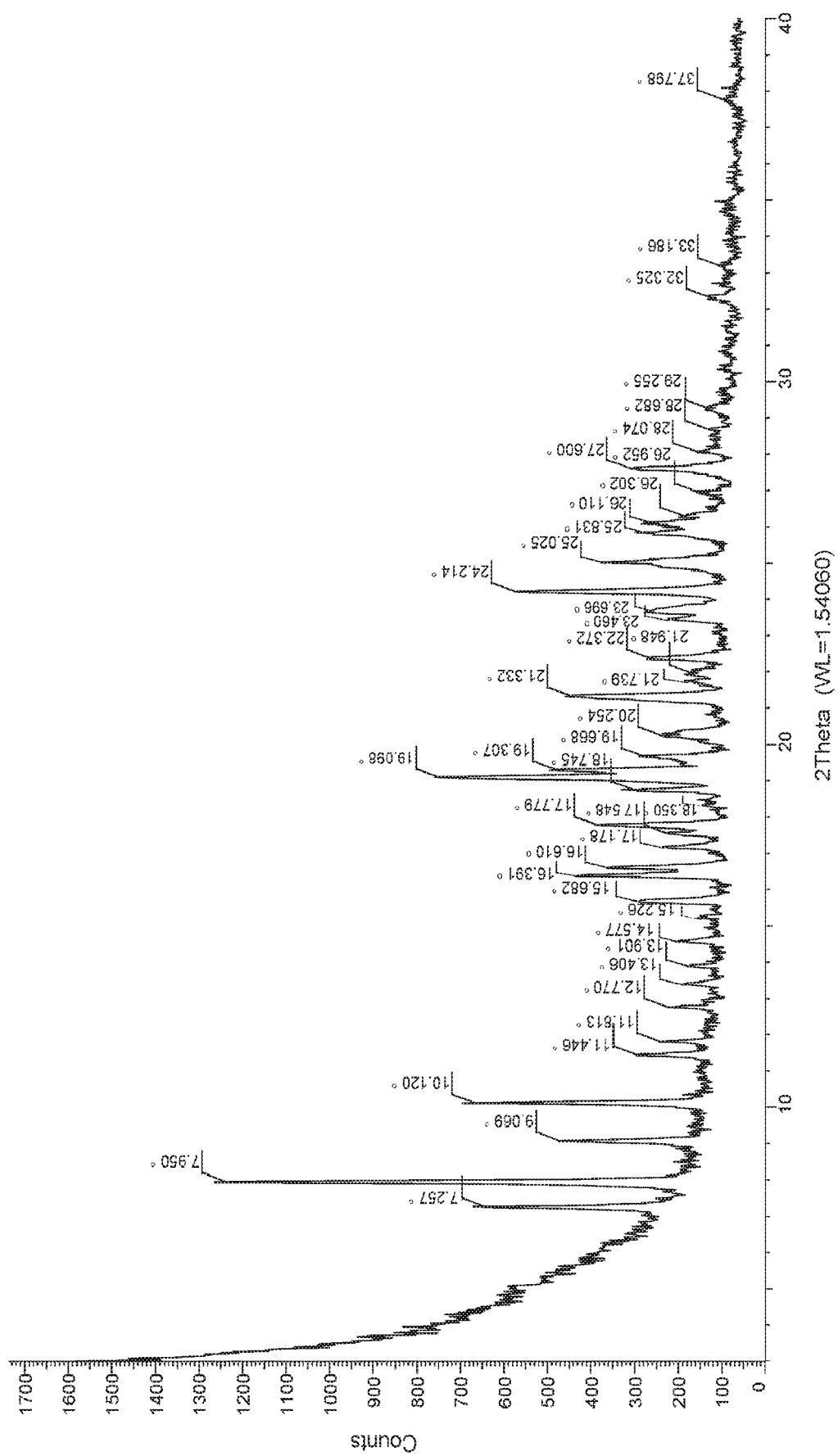
FIG. 17 shows an X-ray powder diffractogram (XRPD) of 9-ING-41 Solvate 2.

In other aspects of the present disclosure, the solid form of 9-ING-41 is 9-ING-41 Solvate 2. In other aspects, the solid form is 9-ING-41 Solvate 2 substantially free of any other solid form of 9-ING-41. 9-ING-41 Solvate 2 can be characterized by an XRPD substantially as shown in FIG. 17.

The XRPD of 9-ING-41 Solvate 2 shown in FIG. 17 comprises reflection angles (degrees 2-theta±0.2 degrees 2-theta), line spacings (d Values), and relative intensities shown in Table 8 below:

TABLE 8

XRPD Data for Solvate 2

| Angle (degrees 2-theta ± 0.2 degrees 2-theta) | d Value (Å) | Relative Intensity |
|---|---|---|
| 7.257 | 12.17130 | 39.4% |
| 7.950 | 11.11181 | 100.0% |
| 9.069 | 9.74359 | 29.4% |
| 10.120 | 8.73398 | 49.9% |
| 11.446 | 7.72466 | 15.6% |
| 11.813 | 7.48553 | 10.8% |
| 12.770 | 6.92647 | 10.2% |
| 13.406 | 6.59952 | 7.1% |
| 13.901 | 6.36563 | 6.2% |
| 14.577 | 6.07180 | 8.8% |
| 15.226 | 5.81446 | 3.9% |
| 15.682 | 5.64641 | 17.6% |
| 16.391 | 5.40361 | 30.8% |
| 16.610 | 5.33285 | 24.6% |
| 17.178 | 5.15789 | 12.7% |
| 17.548 | 5.05001 | 11.8% |
| 17.779 | 4.98467 | 27.0% |
| 18.350 | 4.83103 | 3.2% |
| 18.745 | 4.73009 | 18.5% |
| 19.098 | 4.64348 | 61.1% |
| 19.307 | 4.59362 | 35.4% |
| 19.668 | 4.50998 | 16.2% |
| 20.254 | 4.38083 | 12.8% |

TABLE 8-continued

XRPD Data for Solvate 2

| Angle (degrees 2-theta ± 0.2 degrees 2-theta) | d Value (Å) | Relative Intensity |
|---|---|---|
| 21.332 | 4.16186 | 32.5% |
| 21.739 | 4.08487 | 7.0% |
| 21.948 | 4.04641 | 5.9% |
| 22.372 | 3.97073 | 15.4% |
| 23.460 | 3.78890 | 11.7% |
| 23.696 | 3.75177 | 15.2% |
| 24.214 | 3.67262 | 45.0% |
| 25.025 | 3.55546 | 25.3% |
| 25.831 | 3.44628 | 15.8% |
| 26.110 | 3.41016 | 14.9% |
| 26.302 | 3.38570 | 8.4% |
| 26.952 | 3.30549 | 5.9% |
| 27.600 | 3.22931 | 20.9% |
| 28.074 | 3.17587 | 6.5% |
| 28.682 | 3.10992 | 4.0% |
| 29.255 | 3.05027 | 4.3% |
| 32.325 | 2.76722 | 5.7% |
| 33.186 | 2.69743 | 3.2% |
| 37.798 | 2.37819 | 4.5% |

In some embodiments of the present disclosure, 9-ING-41 Solvate 2 is characterized by an XRPD pattern comprising a peak at one of the angles listed in Table 8 above.

In some embodiments, 9-ING-41 Solvate 2 is characterized by an XRPD pattern comprising a peak at 8.0 degrees±0.2 degrees 2-theta. In other embodiments, 9-ING-41 Solvate 2 is characterized by an XRPD pattern comprising one, two, three, four, five, six, seven, or eight peaks selected from 7.3, 8.0, 9.1, 10.1, 19.1, 19.3, 21.3, and 24.2±0.2 degrees 2-theta.

Figure 18:
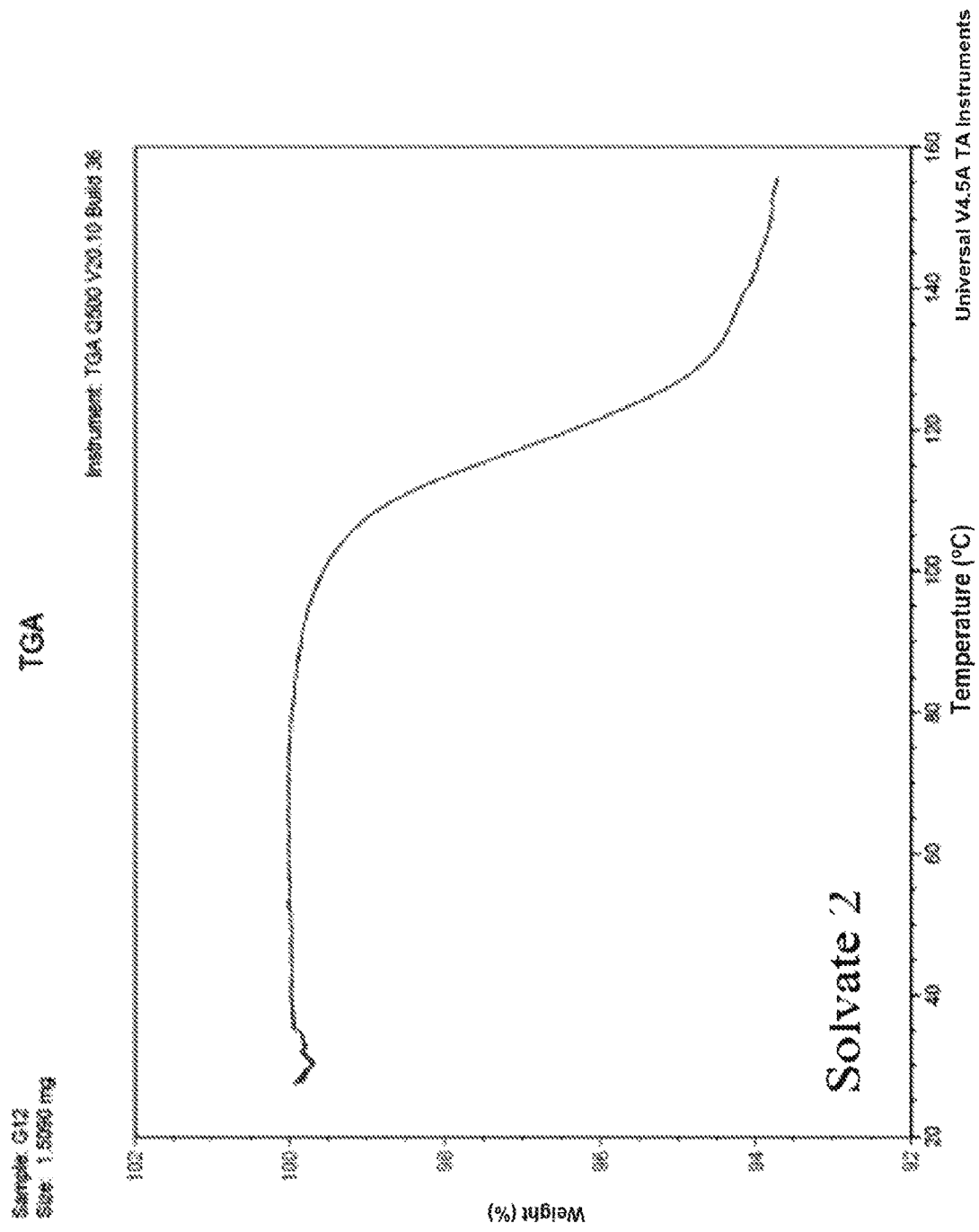
FIG. 18 shows a thermogravimetric analysis (TGA) profile of 9-ING-41 Solvate 2.

9-ING-41 Solvate 2 can be characterized by a TGA profile substantially as shown in FIG. 18 when heated at a rate of 10° C./min. As FIG. 18 shows, Solvate 1 lost approximately 6% by weight upon heating between 90° C. and 150° C. when heated at a rate of 10° C./min.

Figure 19:
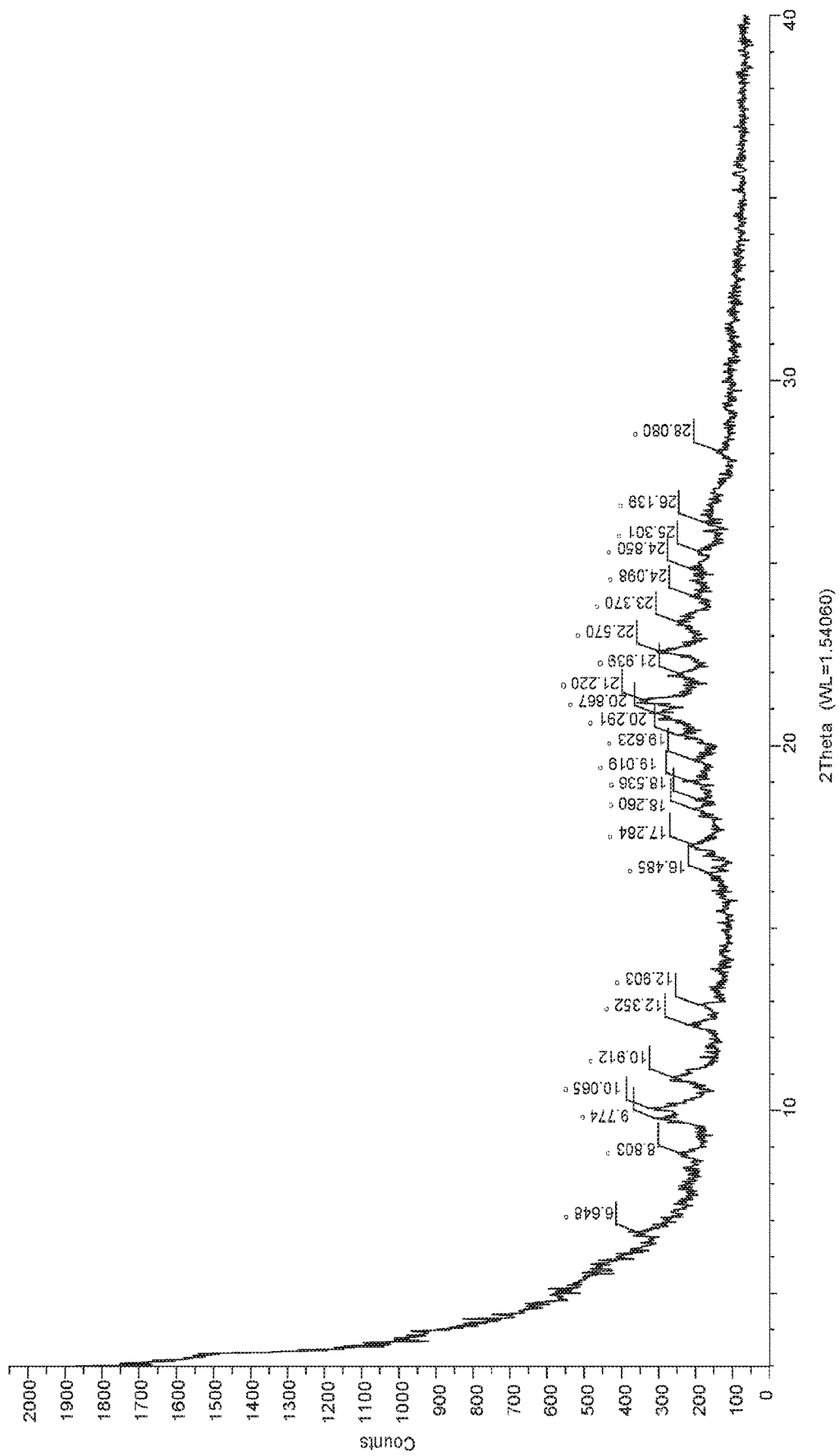
FIG. 19 shows an X-ray powder diffractogram (XRPD) of 9-ING-41 Solvate 4.

In other aspects of the present disclosure, the solid form of 9-ING-41 is 9-ING-41 Solvate 4. In other aspects, the solid form is 9-ING-41 Solvate 4 substantially free of any other solid form of 9-ING-41. 9-ING-41 Solvate 4 can be characterized by an XRPD substantially as shown in FIG. 19.

The XRPD of 9-ING-41 Solvate 4 shown in FIG. 19 comprises reflection angles (degrees 2-theta±0.2 degrees 2-theta), line spacings (d Values), and relative intensities shown in Table 9 below:

TABLE 9

XRPD Data for Solvate 4

| Angle (degrees 2-theta ± 0.2 degrees 2-theta) | d Value (Å) | Relative Intensity |
|---|---|---|
| 6.648 | 13.28468 | 29.8% |
| 8.803 | 10.03701 | 29.7% |
| 9.774 | 9.04171 | 81.2% |
| 10.065 | 8.78084 | 95.7% |
| 10.912 | 8.10167 | 63.9% |
| 12.352 | 7.16027 | 50.1% |
| 12.903 | 6.85559 | 37.0% |
| 16.485 | 5.37310 | 26.2% |
| 17.284 | 5.12629 | 48.7% |
| 18.260 | 4.85468 | 35.1% |
| 18.536 | 4.78289 | 27.8% |
| 19.019 | 4.66253 | 36.7% |

TABLE 9-continued

XRPD Data for Solvate 4

| Angle (degrees 2-theta ± 0.2 degrees 2-theta) | d Value (Å) | Relative Intensity |
|---|---|---|
| 19.623 | 4.52033 | 30.9% |
| 20.291 | 4.37303 | 50.9% |
| 20.867 | 4.25362 | 80.8% |
| 21.220 | 4.18366 | 100.0% |
| 21.939 | 4.04809 | 32.9% |
| 22.570 | 3.93635 | 71.8% |
| 23.370 | 3.80335 | 42.5% |
| 24.098 | 3.69002 | 25.0% |
| 24.850 | 3.58013 | 34.9% |
| 25.301 | 3.51726 | 23.9% |
| 26.139 | 3.40641 | 30.4% |
| 28.080 | 3.17525 | 24.8% |

In some embodiments of the present disclosure, 9-ING-41 Solvate 4 is characterized by an XRPD pattern comprising a peak at one of the angles listed in Table 9 above.

In some embodiments, 9-ING-41 Solvate 4 is characterized by an XRPD pattern comprising a peak at 21.2 degrees±0.2 degrees 2-theta. In other embodiments, 9-ING-41 Solvate 4 is characterized by an XRPD pattern comprising one, two, three, four, five, six, or seven peaks selected from 9.8, 10.1, 10.9, 17.3, 20.9, 21.2, and 22.6±0.2 degrees 2-theta.

Figure 20:
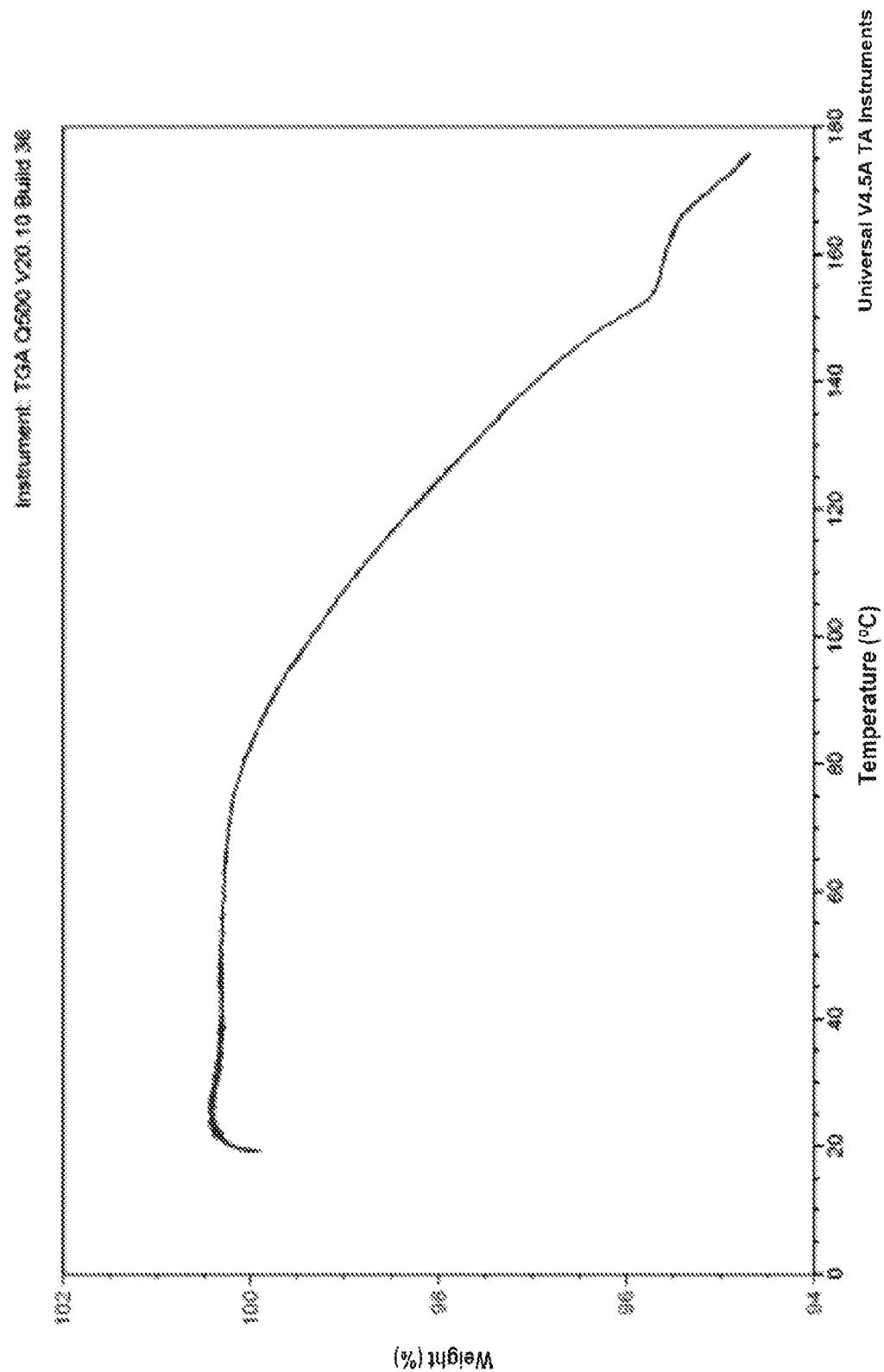
FIG. 20 shows a thermogravimetric analysis (TGA) profile of 9-ING-41 Solvate 4.

9-ING-41 Solvate 4 can be characterized by a TGA profile substantially as shown in FIG. 20 when heated at a rate of 10° C./min. As FIG. 20 shows, Solvate 4 lost approximately 4.5% by weight upon heating between 60° C. and 160° C. when heated at a rate of 10° C./min.

Figure 21:
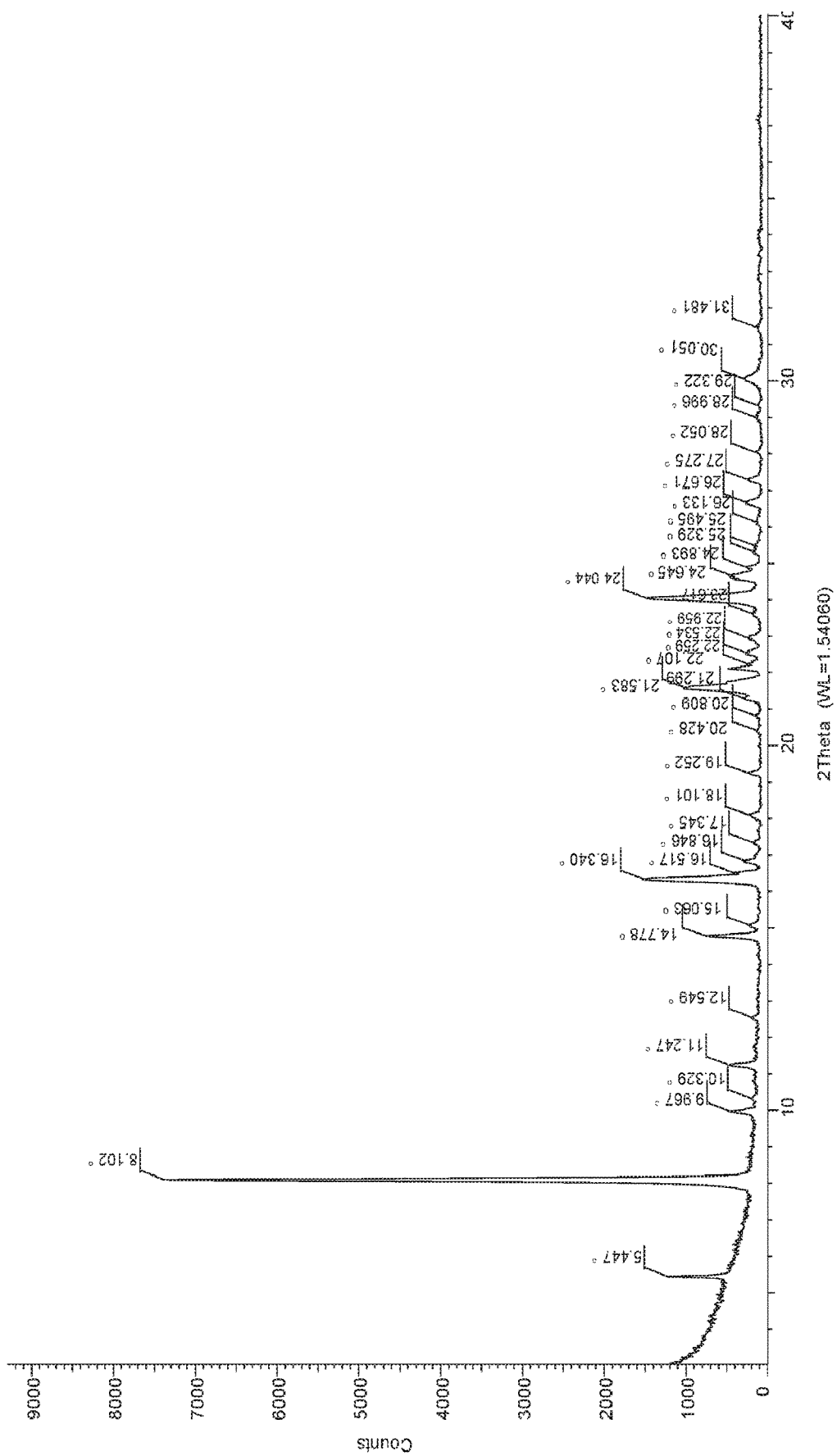
FIG. 21 shows an X-ray powder diffractogram (XRPD) of 9-ING-41 Solvate 5.

In other aspects of the present disclosure, the solid form of 9-ING-41 is 9-ING-41 Solvate 5. In other aspects, the solid form is 9-ING-41 Solvate 5 substantially free of any other solid form of 9-ING-41. 9-ING-41 Solvate 5 can be characterized by an XRPD substantially as shown in FIG. 21.

The XRPD of 9-ING-41 Solvate 5 shown in FIG. 21 comprises reflection angles (degrees 2-theta±0.2 degrees 2-theta), line spacings (d Values), and relative intensities shown in Table 10 below:

TABLE 10

XRPD Data for Solvate 5

| Angle (degrees 2-theta ± 0.2 degrees 2-theta) | d Value (Å) | Relative Intensity |
|---|---|---|
| 5.447 | 16.20985 | 10.4% |
| 8.102 | 10.90342 | 100.0% |
| 9.967 | 8.86726 | 4.1% |
| 10.329 | 8.55723 | 0.6% |
| 11.247 | 7.86076 | 4.6% |
| 12.549 | 7.04818 | 0.9% |
| 14.778 | 5.98979 | 9.2% |
| 15.063 | 5.87698 | 1.5% |
| 16.340 | 5.42038 | 19.6% |
| 16.517 | 5.36276 | 4.3% |
| 16.846 | 5.25883 | 2.4% |
| 17.345 | 5.10862 | 1.1% |
| 18.101 | 4.89690 | 2.0% |
| 19.252 | 4.60649 | 2.0% |
| 20.428 | 4.34393 | 0.7% |
| 20.809 | 4.26528 | 0.6% |
| 21.299 | 4.16830 | 2.7% |
| 21.583 | 4.11410 | 12.5% |
| 22.107 | 4.01775 | 5.1% |

TABLE 10-continued

XRPD Data for Solvate 5

| Angle (degrees 2-theta ± 0.2 degrees 2-theta) | d Value (Å) | Relative Intensity |
|---|---|---|
| 22.259 | 3.99069 | 2.1% |
| 22.534 | 3.94256 | 2.1% |
| 22.959 | 3.87051 | 2.0% |
| 23.617 | 3.76420 | 1.2% |
| 24.044 | 3.69818 | 19.2% |
| 24.645 | 3.60941 | 4.2% |
| 24.893 | 3.57398 | 2.2% |
| 25.329 | 3.51351 | 0.9% |
| 25.495 | 3.49101 | 0.9% |
| 26.133 | 3.40721 | 0.7% |
| 26.671 | 3.33965 | 2.3% |
| 27.275 | 3.26706 | 1.9% |
| 28.052 | 3.17827 | 1.1% |
| 28.996 | 3.07689 | 0.9% |
| 29.322 | 3.04346 | 0.5% |
| 30.051 | 2.97125 | 2.8% |
| 31.481 | 2.83952 | 0.9% |

In some embodiments of the present disclosure, 9-ING-41 Solvate 5 is characterized by an XRPD pattern comprising a peak at one of the angles listed in Table 10 above.

In some embodiments, 9-ING-41 Solvate 5 is characterized by an XRPD pattern comprising a peak at 8.1 degrees±0.2 degrees 2-theta. In other embodiments, 9-ING-41 Solvate 4 is characterized by an XRPD pattern comprising one, two, three, four, five, or six peaks selected from 5.4, 8.1, 14.8, 16.3, 21.6, and 24.0±0.2 degrees 2-theta.

9-ING-41 Solvate 5 can be characterized by a TGA profile substantially as shown in FIG. 22 when heated at a rate of 10° C./min. As FIG. 22 shows, Solvate 1 lost approximately 2.5% by weight upon heating between 115° C. and 130° C. when heated at a rate of 10° C./min.

In some aspects, the present disclosure is directed to amorphous 9-ING-41. Amorphous 9-ING-41 is characterized by the absence of discernable peaks in an XRPD diffractogram.

In some aspects, the present disclosure is directed to processes for preparing the disclosed solid forms of 9-ING-41. In some aspects, the process comprises concentrating a solution of 9-ING-41 dissolved in a solvent or mixture of solvents.

In some aspects, the present disclosure pertains to processes for preparing Crystalline Form I of 9-ING-41. In some embodiments, the process comprises the step of concentrating (e.g., in vacuo or via evaporation) a solution of 9-ING-41 dissolved in a mixture of ethyl acetate/dichloromethane/petroleum ether. In some embodiments, the ratio of volumes of ethyl acetate to dichloromethane to petroleum ether is about 1:1:5.

In other embodiments, the process for preparing Crystalline Form I of 9-ING-41 comprises the step of concentrating (e.g., in vacuo or via evaporation) a solution of 9-ING-41, wherein said solution is a solution of 9-ING-41 in ethyl acetate; 2-propanol/ethyl acetate in a ratio of volumes of about 1:1; 2-methyl-1-propanol/ethyl acetate in a ratio of volumes of about 1:1; 1-butanol/ethyl acetate in a ratio of volumes of about 1:1; 3-methylbutanol/tetrahydrofuran (THF) in a ratio of volumes of about 1:1; 3-methylbutanol/ethyl acetate in a ratio of volumes of about 1:1; THF/water in a ratio of volumes of about 1:1; acetonitrile/water in a ratio of volumes of about 1:1; methyl t-butyl ether (MTBE)/ethyl acetate in a ratio of volumes of about 1:1; or water/ethyl acetate in a ratio of volumes of about 1:1.

In yet other embodiments, the process for preparing Crystalline Form I of 9-ING-41 comprises heating one or more of Solvates 1-9 at a sufficient temperature and for a sufficient time to remove the solvent and to produce the Form I.

The present disclosure also encompasses processes for preparing 9-ING-41 solvates, and in particular Solvates 1-9. In some embodiments, the process for preparing 9-ING-41 Solvate 6 comprises the step of concentrating (e.g., in vacuo or via evaporation) a solution of 9-ING-41 in ethanol/acetone in a ratio of volumes of about 1:1, or ethanol/ethyl acetate in a ratio of volumes of about 1:1. In other embodiments, the process for preparing 9-ING-41 Solvate 6 comprises the step of slurrying 9-ING-41 Form I in ethanol.

In other embodiments, the process for preparing 9-ING-41 Solvate 7 comprises the step of concentrating (e.g., in vacuo or via evaporation) a solution of 9-ING-41 in methanol/THF in a ratio of volumes of about 1:1; methanol/acetonitrile in a ratio of volumes of about 1:1; methanol/MTBE in a ratio of volumes of about 1:1; methanol/acetone in a ratio of volumes of about 1:1; and methanol/ethyl acetate in a ratio of volumes of about 1:1. In other embodiments, the process for preparing 9-ING-41 Solvate 7 comprises the step of slurrying 9-ING-41 Form I in methanol.

In other embodiments, the process for preparing 9-ING-41 Solvate 8 comprises the step of slurrying 9-ING-41 Form I in ethyl acetate.

In other embodiments, the process for preparing 9-ING-41 Solvate 9 comprises the step of concentrating (e.g., in vacuo or via evaporation) a solution of 9-ING-41 in acetone, acetonitrile/acetone in a ratio of volumes of about 1:1; MTBE/acetone in a ratio of volumes of about 1:1; or acetone/water in a ratio of volumes of about 1:1. In other embodiments, the process for preparing 9-ING-41 Solvate 8 comprises the step of slurrying 9-ING-41 Form I in acetone.

In other embodiments, the process for preparing 9-ING-41 Solvate 3 comprises the step of concentrating (e.g., in vacuo or via evaporation) a solution of 9-ING-41 in 2-methyl-1-propanol/acetone in a ratio of volumes of about 1:1; or 1-butanol/acetone in a ratio of volumes of about 1:1.

In other embodiments, the process for preparing 9-ING-41 Solvate 1 comprises the step of concentrating (e.g., in vacuo or via evaporation) a solution of 9-ING-41 in acetone/ethyl acetate in a ratio of volumes of about 1:1. In other embodiments, the process for preparing 9-ING-41 Solvate 2 comprises the step of concentrating a solution of 9-ING-41 in acetone/toluene in a ratio of volumes of about 1:1. In other embodiments, the process for preparing 9-ING-41 Solvate 4 comprises the step of concentrating a solution of 9-ING-41 in 2-propanol/THF in a ratio of volumes of about 1:1. In other embodiments, the process for preparing 9-ING-41 Solvate 5 comprises the step of concentrating a solution of 9-ING-41 in 2-propanol/acetone in a ratio of volumes of about 1:1.

The present disclosure also encompasses processes for preparing amorphous 9-ING-41. In some embodiments, amorphous 9-ING-41 is prepared by a process that comprises the step of rapidly cooling of molten 9-ING-41 to about 0° C. In other embodiments, amorphous 9-ING-41 is prepared by a process that comprises the steps of heating 9-ING-41 to the about 260° C. at the rate of 10° C./min, then cooling the sample down to about −40° C. and then re-heating to about 260° C. at 10° C./min, and then cooling down to about 40° C. In yet other embodiments, amorphous 9-ING-41 is prepared by a process comprising the step of concentrating (e.g., in vacuo or via evaporation) a solution of 9-ING-41 in: ethanol/acetonitrile in a ratio of volumes of about 1:1; ethanol/toluene in a ratio of volumes of about 1:1; 2-propanol/acetonitrile in a ratio of volumes of about 1:1; 2-methyl-1-propanol/acetonitrile in a ratio of volumes of about 1:1, or MTBE/toluene in a ratio of volumes of about 1:1.

In another aspect, the present disclosure encompasses pharmaceutical compositions comprising a solid form of 9-ING-41 of the present disclosure and at least one pharmaceutically acceptable excipient. Pharmaceutically acceptable excipients will be known to those of skill in the art. The pharmaceutical compositions may be administered in any convenient dosage form. Representative dosage forms include tablets, capsules, caplets, reconstitutable powders, elixirs, liquids, colloidal or other types of suspensions, emulsions, beads, beadlets, granules, microparticles, nanoparticles, and combinations thereof. The amount of composition administered will be dependent on the subject being treated, the subject's weight, the severity of the condition being treated, the manner of administration, and the judgment of the prescribing physician. In some embodiments, the pharmaceutical composition comprises crystalline Form I of 9-ING-41 and at least one pharmaceutically acceptable excipient.

The present disclosure also encompasses sterile aqueous or organic solution formulations of 9-ING-41 in which the formulation is prepared from a solid form of 9-ING-41 of the present disclosure. Thus, in some aspects, the present disclosure comprises a process of preparing a pharmaceutical composition that is a solution comprising 9-ING-41. In some embodiments, the method of preparing a pharmaceutical composition comprising a solution of 9-ING-41 comprises dissolving a solid form of 9-ING-41 of the present disclosure in a solvent or mixture of solvents. In some embodiments, the method comprises dissolving crystalline Form I of 9-ING-41 in an aqueous solvent, a non-aqueous solvent, or a mixture of aqueous and/or non-aqueous solvents. The aqueous solvent, non-aqueous solvent, or mixture of aqueous and/or non-aqueous solvents in the embodiments may contain other dissolved ingredients, such as for example, polyethylene glycols, benzyl alcohol, polysorbates, tocopheryl polyethylene glycol succinates, as well as other surfactants, solubilizers, or other pharmaceutically acceptable excipients. Thus, in some embodiments, the process comprises dissolving 9-ING-41 crystalline Form I in an aqueous solvent.

The solid state forms of 9-ING-41 as defined herein, as well as the pharmaceutical compositions or formulations thereof, can be used as medicaments, particularly for the treatment of cancer, including brain, lung, breast, ovarian, bladder, neuroblastoma, renal, and pancreatic cancers, as well as for treatment of traumatic brain injury.

Having described the disclosure with reference to certain preferred embodiments, other embodiments will become apparent to one skilled in the art from consideration of the specification. The disclosure is further illustrated by reference to the following examples. It will be apparent to those skilled in the art that many modifications, both to materials and methods, may be practiced without departing from the scope of the disclosure.

ANALYTICAL METHODS

XRPD Analysis

XRPD analyses were performed using an X-ray diffractometer (Bruker D8 advance) equipped with LynxEye detector. The instrument parameters were listed below.
Scan: 3° (2θ) to 40° (2θ)
Increment: 0.02° (2θ)
Scan speed: 0.3 sec/step
Voltage: 40 KV
Current: 40 mA
Rotation: On
Sample hold: Zero-background sample holder TGA Analysis TGA analyses were carried out on a TA Instruments TGA Q500. Samples was placed in a tarred open aluminum pan and heated from room temperature to the final temperature at a rate of 10° C./min.

DSC Analysis

DSC analyses were conducted on a TA Instruments Q200. A sample in weight was placed into a TA DSC pan, and heated to the final temperature at the rate of 10° C./min.

DVS Analysis

DVS analyses were conducted on an IGAsorp (HidenIsochema Ltd.). For an isotherm test, the chamber temperature was maintained by a water bath at constant 25.0±1.0° C.

HPLC Analysis

The solubility of 9-ING-41 polymorphic forms in water or buffers were determined using HPLC under the following conditions:
Instrument: Agilent 1260 Infinity Series
Diluent: Acetonitrile
Flow rate: 1.5 mL/min
Mobile phase: A: 0.05% TFA in water
  B: 0.05% TFA in Acetonitrile
Injection volume: 1 μL
Column: XDB-C18, 4.6*50 mm, 1.8 μm
Column Temperature: 40° C.
Detection: 220 nm
Run Time: 8 minutes (2 minutes delay for next injection)
Gradient (T/B %): 0.0/70, 6.0/100, 8.0/100

The solubility of 9-ING-41 polymorphic forms in 30% Acetonitrile in water was determined using HPLC under the following conditions:
Instrument: Agilent 1260 Infinity Series
Diluent: 30% acetonitrile aqueous solution
Flow rate: 1.5 mL/min
Mobile phase: A: 0.05% TFA in water
  B: 0.05% TFA in acetonitrile
Injection volume: 5 μL
Column: XDB-C18, 4.6*50 mm, 1.8 μm
Column Temperature: 40° C.
Detection: 220 nm
Run Time: 8 minutes (2 minutes delay for next injection)
Gradient (T/B %): 0.0/70, 6.0/100, 8.0/100

EXAMPLES

Example 1

Preparation of 9-ING-41

Crude 9-ING-41 can be obtained by the general methods described in U.S. Pat. No. 8,207,216, and in Gaisina et al., From a Natural Product Lead to the Identification of Potent and Selective Benzofuran-3-yl-(indol-3-yl)maleimides as Glycogen Synthase Kinase 3β Inhibitors That Suppress Proliferation and Survival of Pancreatic Cancer Cells, *J. Med. Chem.* 2009, 52, 1853-1863.

Example 2

Preparation of 9-ING-41 Crystalline Form I

Crystalline Form I of 9-ING-41 may also be prepared as follows.

Synthesis of Intermediate 1

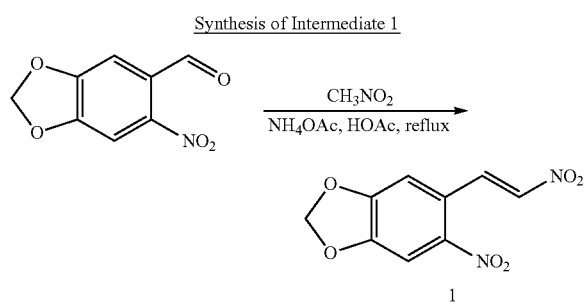

Into a 3-L 4-necked round-bottom flask, purged and maintained with an inert atmosphere of nitrogen, was placed 6-nitro-2H-1,3-benzodioxole-5-carbaldehyde (200 g, 1.02 mol, 1.00 equiv), ammonium acetate (200 g, 2.59 mol, 2.53 equiv), acetic acid (2 L), and nitromethane (313 g, 5.13 mol, 5.00 equiv). The solution was stirred for 12 h at 100° C. The reaction repeated three times. The solutions were combined and diluted with 20 L of water. The resulting solution was extracted with 3×10 L of ethyl acetate and the organic layers were combined. The mixture was washed with 3×10 L of brine, dried over anhydrous sodium sulfate and concentrated under vacuum. This resulted in 450 g (crude) of 5-nitro-6-[(E)-2-nitroethenyl]-2H-1,3-benzodioxole (1) as a dark green solid.

Synthesis of Intermediate 2

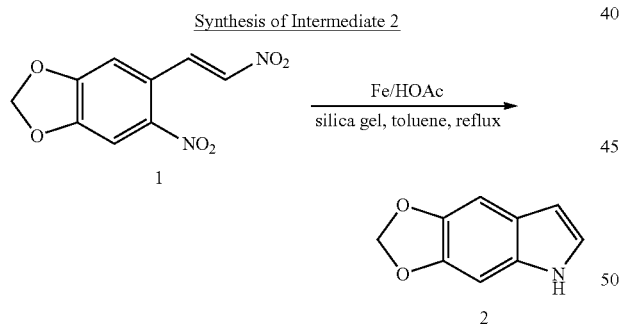

Fe (120 g, 2.14 mol, 17.01 equiv) was slowly added in portions into a suspension of 5-nitro-6-[(Z)-2-nitroethenyl]-2H-1,3-benzodioxole (30 g, 125.97 mmol, 1.00 equiv), silica gel (120 g) in acetic acid (300 mL), toluene (200 mL), and cyclohexane (400 mL) at 80° C. under nitrogen. The resulting black mixture was stirred for 8 h at 80° C. The reaction repeated ten times. The reaction mixtures were combined. The solids were filtrated out. The filtrate was concentrated under vacuum and the residue was applied onto a silica gel column with ethyl acetate/petroleum ether (1/5). The collected fractions were combined and concentrated under vacuum to give 67.3 g (33%) of 2H, 5H-[1, 3] dioxolo [4, 5-f] indole (2) as an off-white solid.

Synthesis of Intermediate 3

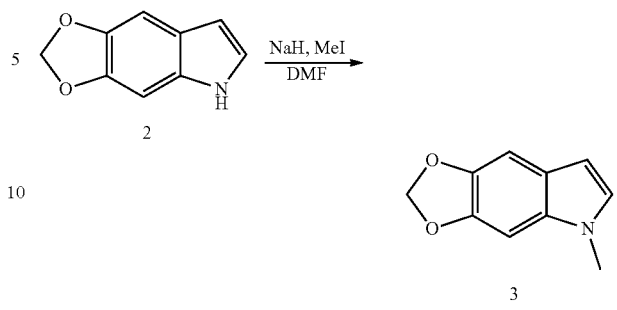

Sodium hydride (19.9 g, 497.50 mmol, 1.18 equiv, 60%) was added in portions into a solution of 2H, 3H,5H-furo[2,3-f]indole (67.3 g, 422.78 mmol, 1.00 equiv) in N,N-dimethylformamide (1.3 L) at 0° C. under nitrogen. The mixture was stirred for 1 h at 0° C. and CH$_3$I (70.9 g, 499.51 mmol, 1.18 equiv) was added dropwise. The resulting solution was stirred for 3 h at room temperature. The solution was quenched by added 1 L of ice water. The resulting solution was extracted with 3×1 L of ethyl acetate and the organic layers were combined. The mixture was washed with 3×1 L of brine, dried over anhydrous sodium sulfate and concentrated under vacuum. The residue was applied onto a silica gel column with ethyl acetate/petroleum ether (1/10). The collected fractions were combined and concentrated under vacuum to give 71 g (97%) of 5-methyl-2H, 3H,5H-furo[2,3-f]indole (3) as a light yellow solid.

Synthesis of Intermediate 4

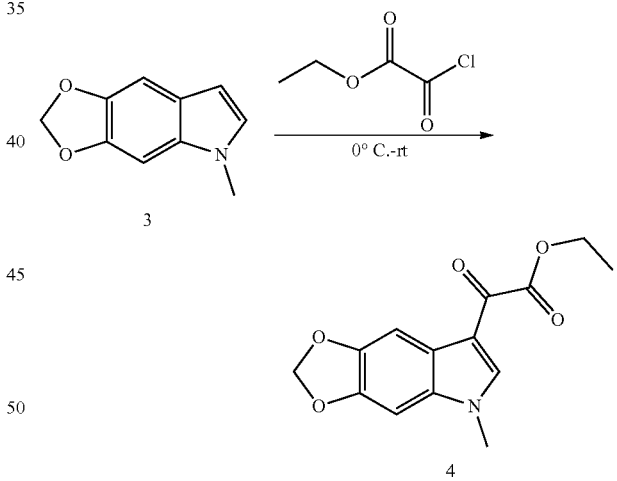

Ethyl 2-chloro-2-oxoacetate (220 g, 1.61 mol, 3.96 equiv) was added dropwise into a solution of 5-methyl-2H,3H,5H-furo[2,3-f]indole (70.4 g, 406.44 mmol, 1.00 equiv) in ethyl ether (1.6 L) at 0° C. under nitrogen. The resulting solution was warmed to room temperature and stirred for 4 h. The reaction was quenched slowly by the addition of 2 L of ice water and the pH value of the resulting solution was adjusted to 9 by Na$_2$CO$_3$. The resulted mixture was extracted with 3×1.5 L of ethyl acetate. The organic layers were combined and dried over anhydrous sodium sulfate and concentrated under vacuum to give 92.8 g (84%) of ethyl 2-[5-methyl-2H,3H,5H-furo[2,3-f]indol-7-yl]-2-oxoacetate (4) as a light yellow solid.

1H NMR (300 MHz, DMSO-d6): δ 8.28 (s, 4H), 7.56 (s, 4H), 7.27 (s, 4H), 6.17 (s, 1H), 6.08 (s, 8H), 4.35 (q, J=7.1 Hz, 7H), 3.85 (s, 11H), 3.35 (s, 2H), 1.35 (t, J=7.1 Hz, 11H), 1.25 (s, 2H).

Synthesis of Intermediate 5

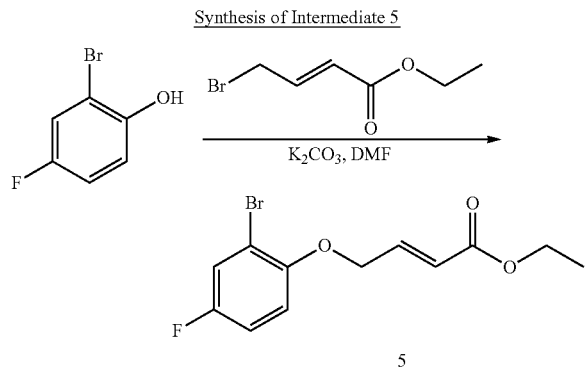

Into a 10-L 4-necked round-bottom flask was placed 2-bromo-4-fluorophenol (500 g, 2.62 mol, 1.00 equiv), N,N-dimethylformamide (5 L), potassium carbonate (1253 g, 9.07 mol, 3.46 equiv), and ethyl (2E)-4-bromobut-2-enoate (1010 g, 5.23 mol, 2.00 equiv). The resulting solution was stirred for 12 h at room temperature. The solids were collected by filtration. The reaction was then quenched by the addition of 15 L of water and extracted with 3×10 L of ethyl acetate. The organic layers were combined and washed with 4×20 L of brine. The mixture was dried over anhydrous sodium sulfate and concentrated under vacuum. The residue was applied onto a silica gel column with ethyl acetate/petroleum ether (1/20). The collected fractions were combined and concentrated under vacuum to give 500 g (63%) of ethyl (2E)-4-(2-bromo-4-fluorophenoxy)but-2-enoate (5) as a white solid.

Synthesis of Intermediate 6

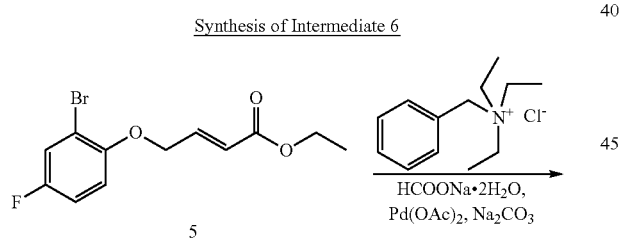

Into a 2-L 3-necked round-bottom flask, purged and maintained with an inert atmosphere of nitrogen, was placed ethyl (2E)-4-(2-bromo-4-fluorophenoxy)but-2-enoate (125 g, 412.37 mmol, 1.00 equiv), benzyltriethylazanium chloride (99 g, 434.64 mmol, 1.05 equiv), sodium formate dihydrate (45.1 g), Pd(OAc)₂ (2.9 g, 12.92 mmol, 0.03 equiv), sodium carbonate (92 g, 868.01 mmol, 2.10 equiv), and N,N-dimethylformamide (1.25 L). The resulting solution was stirred for 12 h at 80° C. The reaction repeated four times. The reaction mixtures were combined and the solids were filtrated out. The filtrate was diluted with 10 L of brine and extracted with 3×5 L of ethyl acetate. The organic layers were combined and washed with 4×6 L of brine. The mixture was dried over anhydrous sodium sulfate and concentrated under vacuum. The residue was applied onto a silica gel column with ethyl acetate/petroleum ether (1/20). The collected fractions were combined and concentrated under vacuum. This resulted in 258 g (crude) of ethyl 2-(5-fluoro-1-benzofuran-3-yl)acetate (6) as light yellow oil.

Synthesis of Intermediate 7

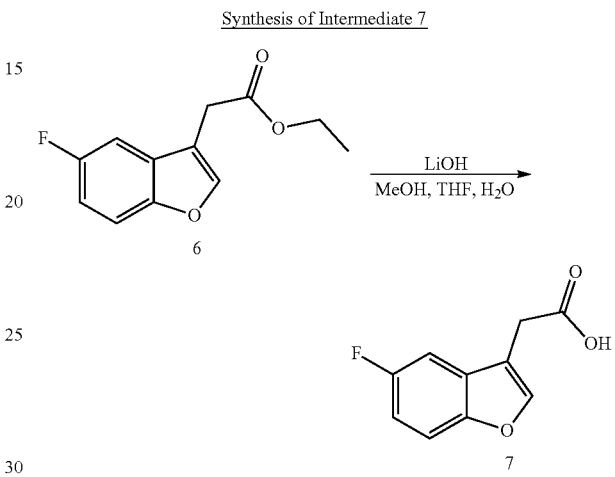

Into a 5-L round-bottom flask was placed ethyl 2-(5-fluoro-1-benzofuran-3-yl)acetate (147 g, 661.53 mmol, 1.00 equiv), methanol (1 L), tetrahydrofuran (1 L), water (1 L), and LiOH (47.7 g, 1.99 mol, 3.01 equiv). The resulting solution was stirred for 3 h at room temperature. The reaction repeated twice. The mixture was concentrated under vacuum and then extracted with 1 L of dichloromethane. The aqueous layer was collected and the pH of the layer was adjust to 1~3 by hydrogen chloride (1 mol/L). The resulting solution was extracted with 3×1 L of ethyl acetate and the combined organic layers were dried over anhydrous sodium sulfate and concentrated under vacuum. This resulted in 160 g (62%) of 2-(5-fluoro-1-benzofuran-3-yl) acetic acid (7) as a white solid.

Synthesis of Intermediate 8

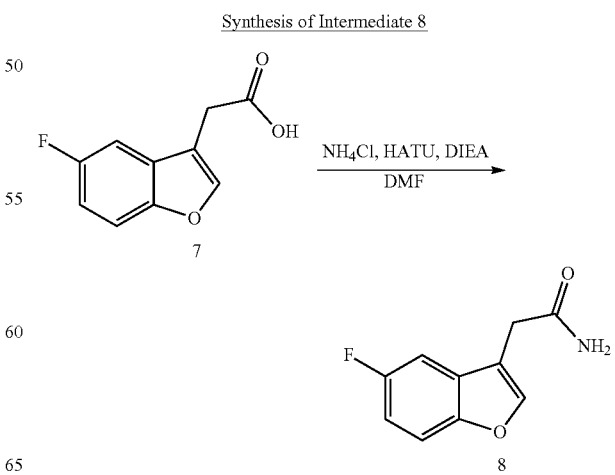

Into a 10-L round-bottom flask was placed 2-(5-fluoro-1-benzofuran-3-yl) acetic acid (160 g, 824.1 mmol, 1.00 equiv), NH4Cl (436 g, 8.16 mol, 9.89 equiv), N,N-dimethylformamide (6L), DIEA (1064 g, 8.24 mol, 9.99 equiv), and HATU (376 g, 988.88 mmol, 1.20 equiv). The resulting solution was stirred for 12 h at room temperature. The resulting solution was diluted with 10 L of water. The solids were collected by filtration to give in 126 g (78%) of 2-(5-fluoro-1-benzofuran-3-yl) acetamide (8) as a white solid.

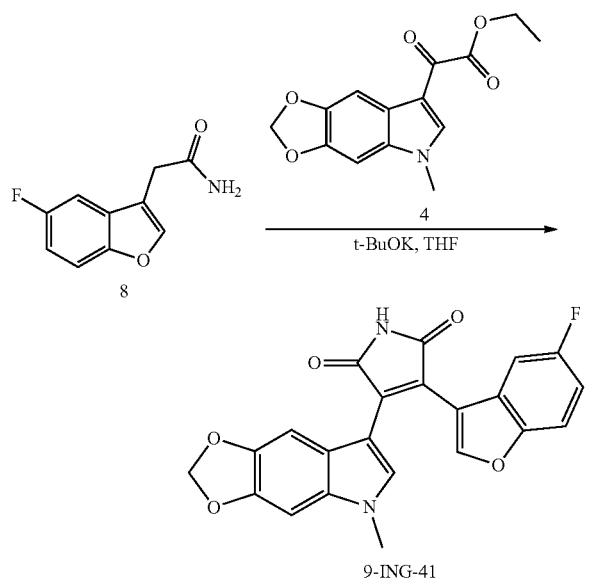

Synthesis of 9-ING-41 in crystalline Form I t-BuOK (1200 mL, 1 mol/L in THF) was added dropwise into a solution of ethyl 2-[5-methyl-2H,3H,5H-furo[2,3-f]indol-7-yl]-2-oxoacetate (100 g, 365.9 mmol, 1.00 equiv), 2-(5-fluoro-1-benzofuran-3-yl)acetamide (72 g, 372.7 mmol, 1.02 equiv) in tetrahydrofuran (3 L) at 0° C. under nitrogen. The reaction was stirred for 2 h at room temperature. The reaction was cooled to 0° C. and poured into of 2 L of NH4Cl (saturated solution in water) and extracted with 4×2 L of dichloromethane. The organic layers were combined, dried over anhydrous sodium sulfate and concentrated under vacuum. The residue was applied onto a silica gel column with ethyl acetate/dichloromethane/petroleum ether (1/1/5). The collected fractions were combined and concentrated under vacuum to give 107.9 g (74%) of 3-(5-fluoro-1-benzofuran-3-yl)-4-[5-methyl-2H,5H-[1,3]dioxolo[4,5-f]indol-7-yl]-2,5-dihydro-1H-pyrrole-2,5-dione as a red solid. This red solid is 9-ING-41 crystalline Form I. MS-ESI: [M+H]+=405.

Example 3

Preparation of 9-ING-41 Crystalline Form I

Crystalline Form I of 9-ING-41 was also prepared by slow evaporation of a solution of 9-ING-41 as follows. About 30-105 mg of 9-ING-41 solid was weighed into glass vials. Each vial was filled with 3 mL of a single solvent. 2 mL of the resulting drug solutions or suspensions were manually filtered into clean glass vials using plastic non-contaminating syringes equipped with 0.22 μm nylon filter cartridges. The resulting filtrates were then either 1) covered with a film with pin hole and evaporated in an operating laboratory fume hood under ambient conditions; or 2) mixed in binary mixtures wherein each mixture contains equal volumes of two different filtrates. The binary mixtures were then covered with a film with pin hole and evaporated in an operating laboratory fume hood under ambient conditions, resulting in solid 9-ING-41 crystalline form I. This procedure was used to prepare 9-ING-41 crystalline form I from the following solvents or solvent mixtures:
  ethyl acetate
  2-propanol:ethyl acetate
  2-methyl-1-propanol:ethyl acetate
  1-butanol:ethyl acetate
  3-methylbutanol:tetrahydrofuran ("THF")
  3-methylbutanol: ethyl acetate
  THF:water
  acetonitrile:water
  methyl t-butyl ether ("MTBE"):ethyl acetate
  water: ethyl acetate Example 4

Preparation of 9-ING-41 Solvate 6

The method set forth above in Example 3 was used to prepare 9-ING-41 Solvate 6 from ethanol:acetone and ethanol:ethyl acetate.

9-ING-41 Solvate 6 was also prepared by slurrying 9-ING-41 Form I in ethanol for three days.

Example 5

Preparation of 9-ING-41 Solvate 7

The method set forth above in Example 3 was used to prepare was used to prepare 9-ING-41 Solvate 7 from methanol/THF; methanol/acetonitrile; methanol/MTBE; methanol/acetone; and methanol/ethyl acetate.

9-ING-41 Solvate 7 was also prepared by slurrying 9-ING-41 Form I in methanol for three days.

Example 6

Preparation of 9-ING-41 Solvate 8

9-ING-41 Solvate 8 was prepared by slurrying 9-ING-41 Form I in ethyl acetate for three days.

Example 7

Preparation of 9-ING-41 Solvate 9

The method set forth above in Example 3 was used to prepare was used to prepare 9-ING-41 Solvate 9 from acetonitrile/acetone, MTBE/acetone; Acetone/water, and pure acetone.

9-ING-41 Solvate 9 was also prepared by slurrying 9-ING-41 Form I in acetone for three days.

Example 8

Preparation of 9-ING-41 Solvate 3

The method set forth above in Example 3 was used to prepare 9-ING-41 Solvate 3 from 2-methyl-1-propanol/acetone; and 1-butanol/acetone.

Example 9

Preparation of 9-ING-41 Solvates 1, 2, 4, and 5

The method set forth above in Example 3 was used to prepare 9-ING-41 Solvates 1, 2, 4, and 5 from the solvents shown below:
Solvate 1: acetone/ethyl acetate
Solvate 2: acetone/toluene
Solvate 4: 2-propanol/THF
Solvate 5: 2-propanol/acetone

Example 10

Aqueous Solubility Studies 10-30 mg of 9-ING-41 Form I was added to 2 mL of water or a buffer solution buffered at pH=1.2, 4.5, or 6.8. The samples were shaken at 200 rpm in a shaker for 24 h. The sample vials were visually examined to ensure saturation. 1 mL of each suspension was filtered at 24 hours through a 0.22 μm nylon syringe filter into another clean clear glass vial. The filtrate was analyzed using HPLC (accurately dilute if necessary) and the remaining solids were analyzed using XRPD.

The solubility of Form I was poor in water, or in pH 1.2, 4.5, or 6.8 buffer. The 9-ING-41 could not be detected in the filtrates by HPLC. Analysis of the remaining solids showed no change in crystalline form over the course of the experiment: the remaining solids in experiments in which Form I was used remained Form I.

Example 11

Solubility In 30% Acetonitrile in Water

About 5 mg of 9-ING-41 Form I was added into 2 mL of 30% acetonitrile/70% water (vol/vol). The sample was shaken at 200 rpm in a shaker for 24 h. The vial was visually examined to ensure saturation. 1 mL of the suspension was filtered through a 0.22 μm nylon syringe filter into another clean clear glass vial at 2 hours and at 24 hours. The filtrates were analyzed using HPLC (accurately dilute if necessary) and the remaining solids were analyzed using XRPD.

The filtrates from the experiments conducted using 9-ING-41 Form I contained 0.046 mg/mL of 9-ING-41 after two hours, and 0.048 mg/mL 9-ING-41 after 24 hours, as determined by HPLC.

Analysis of the remaining solids showed no change in crystalline form over the course of the experiment: the remaining solids in experiments in which Form I was used remained Form I.

Amorphous 9-ING-41 was determined to have a solubility of 0.057 mg/mL in 30% acetonitrile/70% water (vol/vol) after 30 minutes.

Example 13

Mechanical and Pressure Effects 9.90 mg of 9-ING-41 Form I was weighed into mortar and ground for 5 min. The remaining solid was collected and analyzed by XRPD, which showed that the crystalline form (i.e., Form I) had not changed as a result of grinding.

9-ING-41 Form I was pressed into two tablets. The weight of tablets was 38.9 mg and 36.2 mg, respectively. The tablets were then ground into powder and analyzed by XRPD, which showed that the crystalline form (i.e., Form I) had not changed as a result of pressing the 9-ING-41 Form I into tablets.

Example 14

Thermal Treatment—Preparation of Amorphous 9-ING-41

9-ING-41 Form I was heated by DSC to the final temperature of 260° C. at the rate of 10° C./min. The melted product was put into ice bath immediately and held for 15 minutes. The residue was analyzed by XRPD, which showed that the material was amorphous.

9-ING-41 Form I was heated to the final temperature of 260° C. at the rate of 10° C./min, then cooled down to −40° C. and re-heated to 260° C. at the same heating rate, and then cooled down to 40° C. The residue was analyzed by XRPD, which showed that the material was amorphous.

Example 15

Preparation of Amorphous 9-ING-41

The method set forth above in Example 3 was used to prepare amorphous 9-ING-41 from ethanol/acetonitrile; ethanol/toluene; 2-propanol/acetonitrile; 2-methyl-1-propanol/acetonitrile, and MTBE/toluene.

What is claimed:

1. A solid form of 3-(5-fluorobenzofuran-3-yl)-4-(5-methyl-5H-[1,3]dioxolo[4,5-f]indol-7-yl)pyrrole-2,5-dione, characterized by an X-ray powder diffraction pattern comprising a peak at 5.5 degrees±0.2 degrees 2-theta, on the 2-theta scale with lambda=1.54 angstroms (Cu Kα).

2. The solid form of claim 1, characterized by an X-ray powder diffraction pattern as shown in FIG. 1.

3. The solid form of claim 1, characterized by an X-ray powder diffraction pattern comprising peaks at 20.4, 22.1, and 24.7 degrees±0.2 degrees 2-theta, on the 2-theta scale with lambda=1.54 angstroms (Cu Kα).

4. The solid form of claim 1, characterized by an X-ray powder diffraction pattern comprising peaks at 17.7, 18.4, 18.9, and 20.8 degrees±0.2 degree 2-theta, on the 2-theta scale with lambda=1.54 angstroms (Cu Kα).

5. The solid form of claim 1, characterized by an X-ray powder diffraction pattern comprising peaks at 5.5, 9.4, 11.8, 13.4, 15.3, 24.7, and 29.3 degrees±0.2 degree 2-theta, on the 2-theta scale with lambda=1.54 angstroms (Cu Kα).

6. The solid form of claim 1, characterized by an X-ray powder diffraction pattern comprising peaks at three or more of 5.5, 9.4, 11.8, 13.4, 15.3, 17.7, 18.4, 18.9, 20.4, 20.8, 22.1, 24.7, and 29.3, degrees±0.2 degrees 2-theta, on the 2-theta scale with lambda=1.54 angstroms (Cu Kα).

7. The solid form of claim 1, characterized by a differential scanning calorimetry (DSC) thermogram as shown in FIG. 2 when heated at a rate of 10° C./min.

8. The solid form of claim 1, characterized by a differential scanning calorimetry (DSC) thermogram comprising an endothermic peak at about 228° C. when heated at a rate of 10° C./min.

9. The solid form of claim 1, characterized by a thermogravimetric analysis profile as shown in FIG. 3 when heated at a rate of 10° C./min.

10. The solid form of claim 1, characterized by a dynamic vapor sorption (DVS) profile as shown in FIG. 4.

11. A process for preparing the solid form of claim 1, comprising (i) dissolving 3-(5-Fluorobenzofuran-3-yl)-4-(5- methyl-5H-[1,3]dioxolo[4,5-f]indol-7-yl)pyrrole-2,5-dione in a solvent to form a solution; and (ii) concentrating the solution.

12. The process of claim 11, wherein the solvent comprises
   a mixture of ethyl acetate/dichloromethane/petroleum ether in a ratio of volumes of about 1:1:5; ethyl acetate;
   a mixture of 2-propanol/ethyl acetate in a ratio of volumes of about 1:1;
   a mixture of 2-methyl-1-propanol/ethyl acetate in a ratio of volumes of about 1:1; a
   mixture of 1-butanol/ethyl acetate in a ratio of volumes of about 1:1;
   a mixture of 3-methylbutanol/tetrahydrofuran (THF) in a ratio of volumes of about 1:1; a
   mixture of 3-methylbutanol/ethyl acetate in a ratio of volumes of about 1:1;
   a mixture of THF/water in a ratio of volumes of about 1:1;
   a mixture of acetonitrile/water in a ratio of volumes of about 1:1;
   a mixture of methyl t-butyl ether (MTBE)/ethyl acetate in a ratio of volumes of about 1:1; or
   a mixture of water/ethyl acetate in a ratio of volumes of about 1:1.

13. A pharmaceutical composition comprising the solid form of claim 1 and a pharmaceutically acceptable excipient.

14. The pharmaceutical composition of claim 13, further comprising a solid form of 3-(5-fluorobenzofuran-3-yl)-4-(5-methyl-5H-[1,3]dioxolo[4,5-f]indol-7-yl)pyrrole-2,5-dione which is amorphous.

15. A method of treating cancer in a patient comprising administering to a patient in need thereof a therapeutically effective amount of the solid form of claim 1.

16. The method of claim 15, wherein the cancer is brain, lung, breast, ovarian, bladder, neuroblastoma, renal, or pancreatic cancer.

17. A method of treating traumatic brain injury in a patient comprising administering to a patient in need thereof a therapeutically effective amount of the solid form of claim 1.

* * * * *